US012629477B2

(12) United States Patent (10) Patent No.: US 12,629,477 B2
Basham et al. (45) Date of Patent: May 19, 2026

(54) VACUUM INSERTION METHODS FOR INSERTING LUBRICANT FREE SYRINGE STOPPERS AND A SYSTEM FOR ASSEMBLING SAME

(71) Applicant: W. L. Gore & Associates, Inc., Newark, DE (US)

(72) Inventors: Robert Basham, Newark, DE (US); Nicole Dupuy, Newark, DE (US); Erik Larose, Newark, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 916 days.

(21) Appl. No.: 17/912,479

(22) PCT Filed: Mar. 9, 2021

(86) PCT No.: PCT/US2021/021425
§ 371 (c)(1),
(2) Date: Sep. 16, 2022

(87) PCT Pub. No.: WO2021/188319
PCT Pub. Date: Sep. 23, 2021

(65) Prior Publication Data
US 2023/0140221 A1 May 4, 2023

Related U.S. Application Data

(60) Provisional application No. 63/014,938, filed on Apr. 24, 2020, provisional application No. 62/990,032, filed on Mar. 16, 2020.

(51) Int. Cl.
*A61M 5/315* (2006.01)
*B65B 3/00* (2006.01)
(Continued)

(52) U.S. Cl.
CPC ......... *A61M 5/31513* (2013.01); *B65B 3/003* (2013.01); *B65B 7/2821* (2013.01);
(Continued)

(58) Field of Classification Search
CPC ...... A61M 2205/0216; A61M 2207/10; A61M 5/3148; A61M 5/31513; B65B 3/003; B65B 31/027; B65B 7/2821
See application file for complete search history.

(56) References Cited

U.S. PATENT DOCUMENTS

| 5,607,400 A | 3/1997 | Thibault et al. |
| 7,328,549 B2 | 2/2008 | Kinney |
(Continued)

FOREIGN PATENT DOCUMENTS

| CN | 104602738 B | 3/2017 |
| EP | 0743072 A2 | 11/1996 |
(Continued)

OTHER PUBLICATIONS

International Preliminary Report on Patentability received for PCT Patent Application No. PCT/US21/21425, mailed on Sep. 29, 2022, 9 pages.
(Continued)

*Primary Examiner* — Himchan Song
(74) *Attorney, Agent, or Firm* — Faegre Drinker Biddle & Reath LLP

(57) ABSTRACT
Methods of inserting a lubricant free stopper into a lubricant free syringe barrel or lubricant free cartridge tube is disclosed. The method includes (1) inserting a stopper with a sealing rib into a placement region of a vacuum chamber, (2) creating a seal between the vacuum chamber and a syringe barrel or a cartridge tube, (3) maneuvering the stopper into a proximal end of the syringe barrel or cartridge tube by a first differential pressure and/or an insertion rod, (4) maneu-
(Continued)

vering the stopper through the barrel by second differential pressure and/or an insertion rod, (5) optionally sealing a pressure sealing cap to the proximal end of the vacuum chamber, (6) removing the vacuum chamber, insertion rod, and, if present, the pressure sealing cap. The methods are lubricant free or substantially lubricant free. The vacuum chamber may be electropolished and/or extrude honed.

17 Claims, 14 Drawing Sheets

(51) Int. Cl.
B65B 7/28 (2006.01)
B65B 31/02 (2006.01)

(52) U.S. Cl.
CPC ... B65B 31/027 (2013.01); A61M 2205/0216 (2013.01); A61M 2207/10 (2013.01)

(56) References Cited

U.S. PATENT DOCUMENTS

| | | | |
|---|---|---|---|
| 2005/0236063 A1 | 10/2005 | DiGregorio et al. | |
| 2006/0168916 A1* | 8/2006 | Griebel | B65B 3/003 |
| | | | 53/489 |
| 2007/0175538 A1* | 8/2007 | Rothbauer | B65B 3/003 |
| | | | 141/59 |
| 2015/0190578 A1* | 7/2015 | Okihara | B65B 7/2821 |
| | | | 53/111 R |
| 2016/0243311 A1 | 8/2016 | Fournier | |
| 2017/0081056 A1 | 3/2017 | Zambaux et al. | |
| 2019/0328978 A1 | 10/2019 | LaRose | |
| 2025/0339068 A1* | 11/2025 | Ma | A61B 5/150236 |

FOREIGN PATENT DOCUMENTS

| | | | |
|---|---|---|---|
| WO | 2017044112 A1 | 3/2017 | |
| WO | 2019/005072 A1 | 1/2019 | |

OTHER PUBLICATIONS

International Search Report and Written Opinion received for PCT Patent Application No. PCT/US21/21425, mailed on Jun. 24, 2021, 10 pages.

* cited by examiner

VACUUM INSERTION METHODS FOR INSERTING LUBRICANT FREE SYRINGE STOPPERS AND A SYSTEM FOR ASSEMBLING SAME

FIELD

The present invention relates generally to syringes and syringe assemblies, and more particularly, to vacuum insertion methods for the insertion of a lubricant free stopper into a lubricant free barrel (e.g., syringe) or a lubricant free cartridge tube (e.g., cartridge). A system for assembling a lubricant free syringe and a lubricant free cartridge is also provided.

BACKGROUND

Pre-filled syringes function to both store and deliver drugs and/or biologics (e.g., pharmaceutical and/or biopharmaceutical treatments). Also, pre-filled syringes generally offer cost savings to the pharmaceutical industry and may improve the safety, convenience, and efficacy of drug delivery. Biopharmaceuticals are an important class of pharmaceuticals that may increase the use of pre-filled syringes and related devices, such as auto injectors or injectable pens (e.g., EpiPen®). Non-limiting examples of biopharmaceuticals include insulin, vaccines, antibodies, blood products, hormones, and/or cytokines. As more pharmaceuticals and particularly biopharmaceuticals are utilized for delivery in pre-filled syringes and other pre-filled injection devices, difficulties regarding the use of conventional syringe technology in pre-filled injection devices became apparent.

There are several aspects of traditional syringe construction that present a challenge for their use as pre-filled syringes. One is the use of silicone (e.g., silicone oil) and/or other lubricants. Conventionally, silicone provides a liquid seal between the stopper and the syringe barrel. While silicone has traditionally been used to ensure that the force required to actuate a pre-filled syringe or similar pre-filled injectable device is minimized, the use of silicone as a lubricant poses a contamination risk. For example, silicone may degrade or contaminate the drug or biologic within the injectable device. Additionally, the silicone may be injected into a patient along with the drug. Silicone may be of particular concern regarding biopharmaceuticals because it can cause aggregation of certain proteins, thereby rendering the biopharmaceutical unusable for injection.

A second aspect is the occurrence of small bumps or asperities on the inner surface of the syringe barrel or vacuum chamber that may be present as a by-product of the manufacturing processes thereof. Typically, these asperities have no effect on a lubricated stopper as the silicone in the syringe barrel or vacuum chamber allows the stopper to easily pass over the asperities. However, if silicone or other suitable lubricant is not applied or is inadvertently omitted, damage or destruction of the stopper due to the presence of the asperities may result in failure of the syringe or similar injectable device.

Therefore, a need exists for a method of vacuum inserting a lubricant free stopper into a lubricant free barrel or a lubricant free cartridge tube in a manner that both reduces the potential for drug contamination and minimizes damage to the stopper.

SUMMARY

According to one Aspect ("Aspect 1"), a method includes providing a syringe that includes a non-lubricated inner surface and a barrel flange; inserting a non-lubricated stopper that includes a sealing rib into a placement region located at a proximal end of a vacuum chamber, where the non-lubricated stopper is at least partially covered by a polymer layer; creating a seal between a sealing gasket of the vacuum chamber and the barrel flange of the syringe; applying vacuum through a vacuum port fluidly connected to the non-lubricated barrel to translate the stopper through the vacuum chamber from the placement region of the vacuum chamber into a proximal end of the non-lubricated barrel, where the vacuum port is located at a distal end of the vacuum chamber; translating the stopper through the non-lubricated barrel with an insertion rod until a desired headspace between a front edge of the sealing rib and a liquid solution located in the non-lubricated cartridge tube is achieved; retracting the insertion rod away from the vacuum chamber; and retracting the vacuum chamber away from the non-lubricated barrel.

According to another Aspect ("Aspect 2") further to Aspect 1, the non-lubricated stopper includes an elastomeric material having the polymer layer thereon.

According to another Aspect ("Aspect 3") further to Aspect 1 and Aspect 2, the polymer layer includes an expanded fluoropolymer layer.

According to another Aspect ("Aspect 4") further to any of one of Aspects 1 to 3, the expanded fluoropolymer layer includes an expanded polytetrafluoroethylene layer.

According to another Aspect ("Aspect 5") further to any of one of Aspects 1 to 4, including adding the liquid solution to the non-lubricated barrel prior to creating the vacuum seal between the sealing gasket and the barrel flange.

According to another Aspect ("Aspect 6") further to any of one of Aspects 1 to 5, the liquid solution is a therapeutic substance.

According to another Aspect ("Aspect 7") further to any of one of Aspects 1 to 6, the therapeutic substance contains therein a biologic, a therapeutic compound, or a combination thereof.

According to another Aspect ("Aspect 8") further to any of one of Aspects 1 to 7, the vacuum chamber has been electropolished, extrude honed, or a combination thereof.

According to another Aspect ("Aspect 9") further to any of one of Aspects 1 to 8, at least the stopper, the vacuum chamber, the syringe barrel, the barrel flange, and the insertion pin are free or substantially free of lubricants.

According to another Aspect ("Aspect 10") further to any of one of Aspects 1 to 9, the vacuum chamber contains a transition zone having a taper angle for transitioning the non-lubricated stopper from the placement region of the vacuum chamber to the proximal end of the barrel.

According to another Aspect ("Aspect 11") further to Aspect 10, wherein the taper angle is between about 0.1 degree and about 20 degrees.

According to another Aspect ("Aspect 12") further to any of one of Aspects 1 to 11, the desired headspace ranges from about 1 mm to about 25 mm.

According to another Aspect ("Aspect 13") further to any of one of Aspects 1 to 12, the insertion rod includes a pin tip end and the non-lubricated stopper contains therein a cavity to receive the pin tip end.

According to another Aspect ("Aspect 14") further to any of one of Aspects 1 to 13, the vacuum chamber is positioned above and is aligned with the non-lubricated barrel.

According to another Aspect ("Aspect 15") further to any of one of Aspects 1 to 14, including lowering the vacuum chamber to create the vacuum seal with the non-lubricated barrel.

According to another Aspect ("Aspect 16") further to any of one of Aspects 1 to 15, the insertion rod and vacuum chamber are retracted simultaneously.

According to another Aspect ("Aspect 17") further to any of one of Aspects 1 to 15, the insertion rod is retracted prior to retracting the vacuum chamber.

According to one Aspect ("Aspect 18"), a method includes inserting a non-lubricated stopper that includes a sealing rib into a placement region located at a proximal end of a vacuum chamber, where the non-lubricated stopper is at least partially covered by a polymer layer; creating a vacuum seal between the vacuum chamber and an end portion of the non-lubricated cartridge tube; applying vacuum through a vacuum port fluidly connected to the non-lubricated cartridge tube to vacuum seal the vacuum chamber and sealing gasket of the non-lubricated cartridge tube to translate the non-lubricated stopper through the vacuum chamber from the placement region of the vacuum chamber to a proximal end of the non-lubricated cartridge tube, where the vacuum port is located at a distal end of the vacuum chamber; translating the non-lubricated stopper through the non-lubricated cartridge tube with an insertion rod until a desired headspace between a front edge of the sealing rib and a liquid solution located in the non-lubricated cartridge tube is achieved; retracting the insertion rod away from the vacuum chamber; and retracting the vacuum chamber away from the non-lubricated cartridge tube.

According to another Aspect ("Aspect 19") further to Aspect 18, the stopper comprises an elastomeric material having the polymer layer thereon.

According to another Aspect ("Aspect 20") further to Aspect 18 and Aspect 19, the polymer layer includes an expanded fluoropolymer layer.

According to another Aspect ("Aspect 21") further to Aspect 20, the expanded fluoropolymer layer includes an expanded polytetrafluoroethylene layer.

According to another Aspect ("Aspect 22") further to any one of Aspects 18 to 21, including adding the liquid solution to the non-lubricated barrel prior to creating the vacuum seal between the sealing gasket and the end portion of the non-lubricated cartridge tube.

According to another Aspect ("Aspect 23") further to any one of Aspects 18 to 22, the liquid solution is a therapeutic substance.

According to another Aspect ("Aspect 24") further to any one of Aspects 18 to 23, the therapeutic substance contains therein a biologic, a therapeutic compound, or a combination thereof.

According to another Aspect ("Aspect 25") further to any one of Aspects 18 to 24, the vacuum chamber has been electropolished, extrude honed, or a combination thereof.

According to another Aspect ("Aspect 26") further to any one of Aspects 18 to 25, at least the stopper, the vacuum chamber, the cartridge tube, the end portion of the cartridge tube, and the insertion pin are free or substantially free of lubricants.

According to another Aspect ("Aspect 27") further to any one of Aspects 18 to 26, the vacuum chamber includes a transition zone having a taper angle for transitioning the non-lubricated stopper from the placement region of the vacuum chamber to the proximal end of the cartridge tube.

According to another Aspect ("Aspect 28") further to any one of Aspects 18 to 27, the taper angle is between about 0.1 degree and about 20 degrees.

According to another Aspect ("Aspect 29") further to any one of Aspects 18 to 28, the desired headspace is from about 1 mm to about 25 mm.

According to another Aspect ("Aspect 30") further to any one of Aspects 18 to 29, the insertion rod has a flat or substantially flat surface and the non-lubricated stopper is a solid stopper.

According to another Aspect ("Aspect 31") further to any one of Aspects 18 to 30, the vacuum chamber is positioned above and is aligned with the non-lubricated cartridge tube.

According to another Aspect ("Aspect 32") further to any one of Aspects 18 to 31, including lowering the vacuum chamber to create the vacuum seal with the non-lubricated cartridge tube.

According to another Aspect ("Aspect 33") further to any one of Aspects 18 to 32, the insertion rod and vacuum chamber are retracted simultaneously.

According to another Aspect ("Aspect 34") further to any one of Aspects 18 to 32, the insertion rod is retracted prior to retracting the vacuum chamber.

According to one Aspect ("Aspect 35"), a method includes inserting a non-lubricated stopper that includes a sealing rib into a placement region located at a proximal end of a vacuum chamber, where the non-lubricated stopper is at least partially covered by a polymer layer; creating a seal between a sealing gasket of the vacuum chamber and the barrel flange of the syringe; applying vacuum to a headspace by a vacuum port fluidly connected to the non-lubricated barrel to create a vacuum in the headspace, the non-lubricated barrel has therein a liquid solution, where the vacuum port is located at a distal end of the vacuum chamber; translating the non-lubricated stopper through the vacuum chamber from the placement region of the vacuum chamber into a proximal end of the non-lubricated barrel by a first differential pressure created by the vacuum in the headspace; sealing a pressure sealing cap to a proximal end of the vacuum chamber; maneuvering the non-lubricated stopper through the non-lubricated barrel by a second differential pressure created by the vacuum in the headspace and a pressure applied to the non-lubricated stopper until a final headspace is achieved; retracting the pressure sealing cap away from the vacuum chamber; and retracting the vacuum chamber away from the non-lubricated barrel, where the first headspace and the final headspace are each a distance from a liquid surface of the liquid solution to a front edge of the sealing rib of the non-lubricated stopper.

According to another Aspect ("Aspect 36") further to Aspect 35, the pressure is applied to the non-lubricated stopper through a pressure port in the pressure sealing cap.

According to another Aspect ("Aspect 37") further to Aspect 35 or Aspect 36, including lowering the pressure sealing cap, where the pressure sealing cap is positioned above and aligned with the vacuum chamber.

According to another Aspect ("Aspect 38") further to any one of Aspects 35 to 37, including lowering the vacuum chamber to create the seal between the sealing gasket and the barrel flange of the non-lubricated barrel, where the vacuum chamber is positioned above and aligned with the non-lubricated barrel.

According to another Aspect ("Aspect 39") further to any one of Aspects 35 to 38, the polymer layer includes an expanded fluoropolymer layer.

According to another Aspect ("Aspect 40") further to Aspect 39, the expanded fluoropolymer layer includes an expanded polytetrafluoroethylene layer.

According to another Aspect ("Aspect 41") further to any one of Aspects 35 to 40, including adding the liquid solution to the non-lubricated barrel prior to creating the vacuum seal between the sealing gasket and the barrel flange.

According to another Aspect ("Aspect 42") further to any one of Aspects 35 to 41, the liquid solution is a therapeutic substance.

According to another Aspect ("Aspect 43") further Aspect 42, the therapeutic substance contains therein a biologic, a therapeutic compound, or a combination thereof.

According to another Aspect ("Aspect 44") further to any one of Aspects 35 to 43, the vacuum chamber has been electropolished, extrude honed, or a combination thereof.

According to another Aspect ("Aspect 45") further to any one of Aspects 35 to 44, at least the stopper, the vacuum chamber, the barrel, the barrel flange, and the pressure sealing cap are free or substantially free of lubricants.

According to another Aspect ("Aspect 46") further to any one of Aspects 35 to 45, the vacuum chamber contains a transition zone having a taper angle for transitioning the non-lubricated stopper from the placement region of the vacuum chamber to the proximal end of the non-lubricated barrel.

According to another Aspect ("Aspect 47") further to any one of Aspects 35 to 46, the taper angle is between about 0.1 degree and about 20 degrees.

According to another Aspect ("Aspect 48") further to any one of Aspects 35 to 47, wherein the final headspace is from about 1 mm to about 25 mm.

According to another Aspect ("Aspect 49") further to any one of Aspects 35 to 47, the pressure sealing cap and vacuum chamber are retracted simultaneously.

According to another Aspect ("Aspect 50") further to any one of Aspects 35 to 47, the pressure sealing cap is retracted prior to retracting the vacuum chamber.

According to one Aspect ("Aspect 51"), a method includes inserting a non-lubricated stopper that includes a sealing rib into a placement region located at a proximal end of a vacuum chamber, where the non-lubricated stopper is at least partially covered by a polymer layer; creating a seal between a sealing gasket of the vacuum chamber and an end portion of a cartridge tube; applying vacuum to a headspace by a vacuum port fluidly connected to the non-lubricated cartridge tube to create a vacuum in the headspace, the non-lubricated cartridge tube having therein a liquid solution, where the vacuum port is located at a distal end of the vacuum chamber; translating the non-lubricated stopper through the vacuum chamber from the placement region of the vacuum chamber into a proximal end of the non-lubricated cartridge tube by a first differential pressure created by the vacuum in the headspace; sealing a pressure sealing cap to a proximal end of the vacuum chamber; maneuvering the non-lubricated stopper through the non-lubricated cartridge tube by a second differential pressure created by the vacuum in the headspace and a pressure applied to the non-lubricated stopper until a final headspace is achieved; retracting the pressure sealing cap away from the vacuum chamber; and retracting the vacuum chamber away from the non-lubricated cartridge tube, where the first headspace and the final headspace are each a distance from a liquid surface of the liquid solution to a front edge of the sealing rib of the non-lubricated stopper.

According to another Aspect ("Aspect 52"), further to Aspect 51, the pressure is applied to the non-lubricated stopper through a pressure port in the pressure sealing cap.

According to another Aspect ("Aspect 53"), further to Aspect 50 and Aspect 51, including lowering the pressure sealing cap, where the pressure sealing cap is positioned above and aligned with the vacuum chamber.

According to another Aspect ("Aspect 54") further to any one of Aspects 51 to 53, including lowering the vacuum chamber to create the seal between the sealing gasket and the end portion of the non-lubricated cartridge tube, where the vacuum chamber is positioned above and aligned with the non-lubricated cartridge tube.

According to another Aspect ("Aspect 55") further to any one of Aspects 51 to 54, the polymer layer includes an expanded fluoropolymer layer.

According to another Aspect ("Aspect 56") further to Aspect 55, the expanded fluoropolymer layer includes an expanded polytetrafluoroethylene layer.

According to another Aspect ("Aspect 57") further to any one of Aspects 51 to 56, including adding the liquid solution to the non-lubricated cartridge tube prior to creating the vacuum seal between the sealing gasket and the end of the non-lubricated cartridge tube.

According to another Aspect ("Aspect 58") further to any one of Aspects 51 to 57, wherein the liquid solution is a therapeutic substance.

According to another Aspect ("Aspect 59") further to Aspect 58, wherein the therapeutic substance contains therein a biologic, a therapeutic compound, or a combination thereof.

According to another Aspect ("Aspect 60") further to any one of Aspects 51 to 59, the vacuum chamber has been electropolished, extrude honed, or a combination thereof.

According to another Aspect ("Aspect 61") further to any one of Aspects 51 to 60, at least the stopper, the vacuum chamber, the cartridge tube, the end portion, and the pressure sealing cap are free or substantially free of lubricants.

According to another Aspect ("Aspect 62") further to any one of Aspects 51 to 61, the vacuum chamber contains a transition zone having a taper angle for transitioning the non-lubricated stopper from the placement region of the vacuum chamber to the proximal end of the non-lubricated cartridge tube.

According to another Aspect ("Aspect 63"), further to Aspect 62, the taper angle is between about 0.1 degree and about 20 degrees.

According to another Aspect ("Aspect 64") further to any one of Aspects 51 to 63, the final headspace is from about 1 mm to about 25 mm.

According to another Aspect ("Aspect 65") further to any one of Aspects 51 to 64, the pressure sealing cap and vacuum chamber are retracted simultaneously.

According to another Aspect ("Aspect 66") further to any one of Aspects 51 to 64, the pressure sealing cap is retracted prior to retracting the vacuum chamber.

According to one Aspect ("Aspect 67"), a system includes (A) a vacuum chamber having (1) a placement region that has a diameter for receiving a non-lubricated stopper from a stopper feeder, (2) a body that has a diameter that is smaller than the diameter of the placement region, (3) a transition zone having a taper angle for transitioning a syringe stopper from the placement region to the vacuum chamber, and (4) a vacuum port for drawing a vacuum; (B) a syringe barrel or cartridge tube having an inner surface for receiving the stopper from the vacuum chamber and a therapeutic substance from a therapeutic feeder; (C) a mechanism for lowering the vacuum chamber to sealably attach the syringe barrel or cartridge tube to the vacuum chamber; (D) a first pressure member for maneuvering the syringe stopper through the vacuum chamber; (E) a second pressure member for translating the stopper through the syringe barrel or cartridge tube; (F) a first mechanism for removing the vacuum chamber from the syringe barrel or cartridge tube; and (G) a second mechanism for removing a pressure sealing cap or insertion rod from the vacuum chamber, where (A) to (G) forms a system to form a pre-filled syringe or cartridge, and where the system and the pre-filled syringe are lubricant free or substantially lubricant free.

According to another Aspect ("Aspect 68"), further to Aspect 67, the taper angle is between about 1 degree and about 20 degrees.

According to another Aspect ("Aspect 69"), further to Aspect 67 or Aspect 68, the first pressure member is differential pressure, an insertion pin, or a combination thereof.

According to another Aspect ("Aspect 70") further to any one of Aspects 67 to 69, the second pressure member is a differential in pressure between a vacuum in the headspace and a pressure applied to the stopper, or an insertion pin.

According to another Aspect ("Aspect 71") further to any one of Aspects 67 to 70, the vacuum chamber has been electropolished, extrude honed, or a combination thereof.

According to another Aspect ("Aspect 72") further to any one of Aspects 67 to 71, the therapeutic substance contains therein a biologic, a therapeutic compound, or a combination thereof.

According to another Aspect ("Aspect 73") further to any one of Aspects 67 to 72, the stopper includes an elastomeric body and a polymer layer at least partially covering the elastomeric body.

According to another Aspect ("Aspect 74") further to Aspect 73, the polymer layer includes an expanded fluoropolymer.

According to another Aspect ("Aspect 75") further to Aspect 74, wherein the expanded fluoropolymer includes an expanded polytetrafluoroethylene.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the figures should not be construed as limiting. The terms "barrel" and "syringe barrel" may be used interchangeably herein. It is to be appreciated that the terms "non-lubricated" and "lubricant free" may be interchangeably used herein. It is to be noted that the phrase "non-lubricated syringe barrel" and "non-lubricated barrel" may be interchanged with the phrase "non-lubricated cartridge tube" within this disclosure.

The present disclosure is directed to vacuum methods of inserting a non-lubricated stopper having thereon a polymer layer (e.g., an expanded fluoropolymer layer) into a lubricant free barrel or lubricant free cartridge tube through the use of a vacuum chamber and an insertion pin as well as through the use of a vacuum chamber with pressure assistance (and no insertion pin). The stopper includes an elastomeric body and a polymer layer that at least partially covers the elastomeric body. The syringe or cartridge may be pre-filled for storing and delivering a drug or biologic to a patient. As used herein, the term "syringe" or "cartridge" is meant to refer to any device that delivers at least one therapeutic compound (e.g., drug or biologic) via injection with a needle or with a "needleless" system (e.g., a luer system). The syringe or cartridge may be used to administer different therapeutic compounds such as, for example, drugs and biologics, including but not limited to, antibodies, antisense, RNA interference, gene therapy, primary and embryonic stem cells, vaccines, and combinations thereof. The disclosure hereafter equally applies to a syringe or to a cartridge. Numerous types of medical delivery devices are contemplated, such as, for example, a syringe, an auto-injector, and an injectable pen, and are considered to be within the purview of the present disclosure.

Figure 1A:
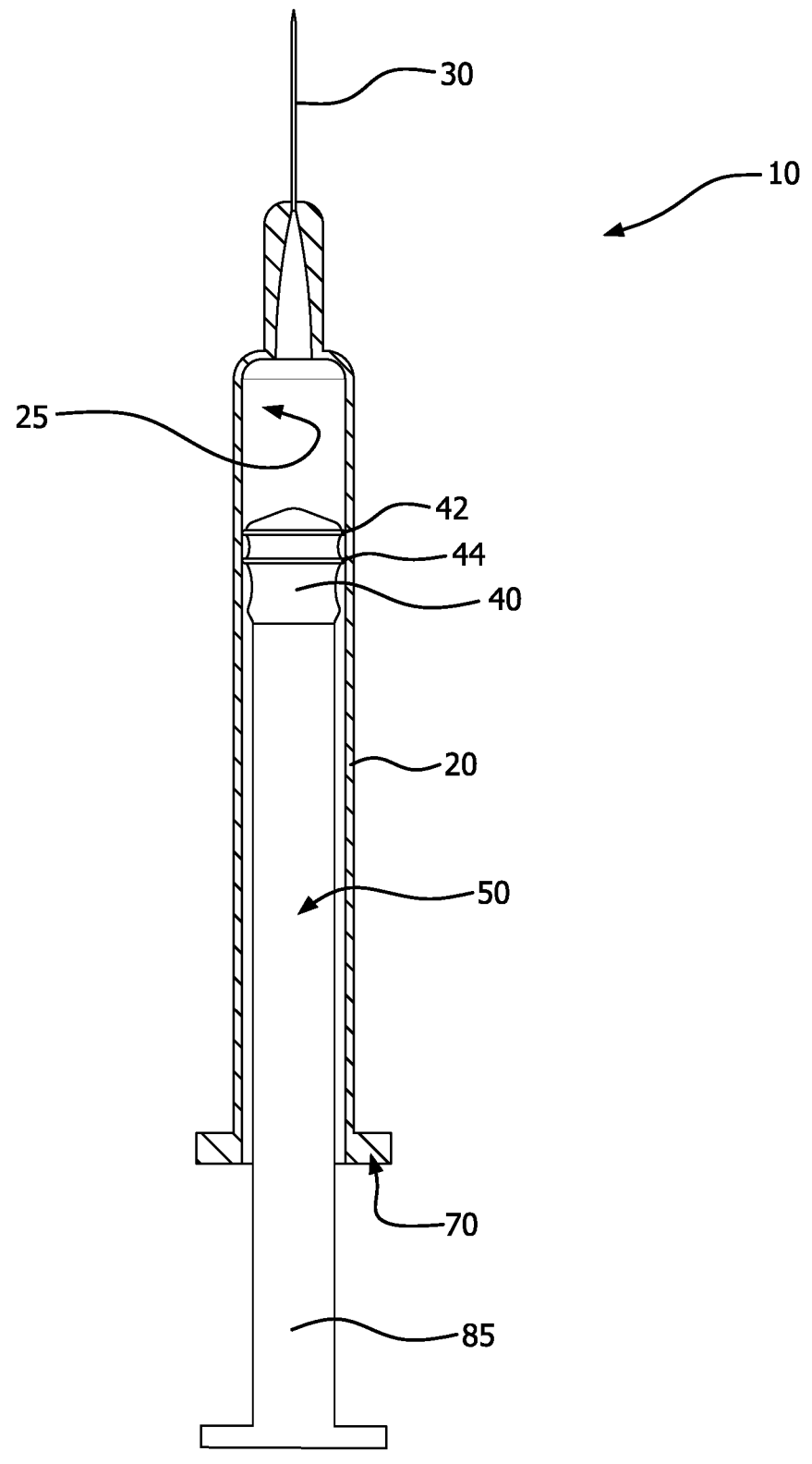
FIG. 1A is a schematic illustration of a syringe in accordance with some embodiments.

As shown in FIG. 1A, the syringe 10 may include a barrel 20 with an inner surface 25, and a piercing element (e.g., needle) 30 attached thereto for injecting a therapeutic compound(s). The plunger 50 is formed of a stopper 40 that may be affixed to an end of a plunger rod 85. In some embodiments, the stopper is not attached to the plunger rod 85 (not illustrated). The stopper 40 contacts at least a portion of the inner surface 25 of the barrel 20 via one or more ribs 42, 44. Although two ribs 42, 44 are shown in FIG. 1A, any number of ribs may be present on the stopper 40 as long as there is at least one sealing rib, such as the front sealing rib 42. In some embodiments, rib 44 may also be a sealing rib. Hereafter, ribs 42, 44 will both be referred to as sealing ribs for ease of discussion. Sealing ribs provide container closure integrity to a pre-filled syringe or cartridge. One or more flanges 70 may be used as a finger grip for pressing and translating the plunger 50 within the barrel 20.

Figure 1B:
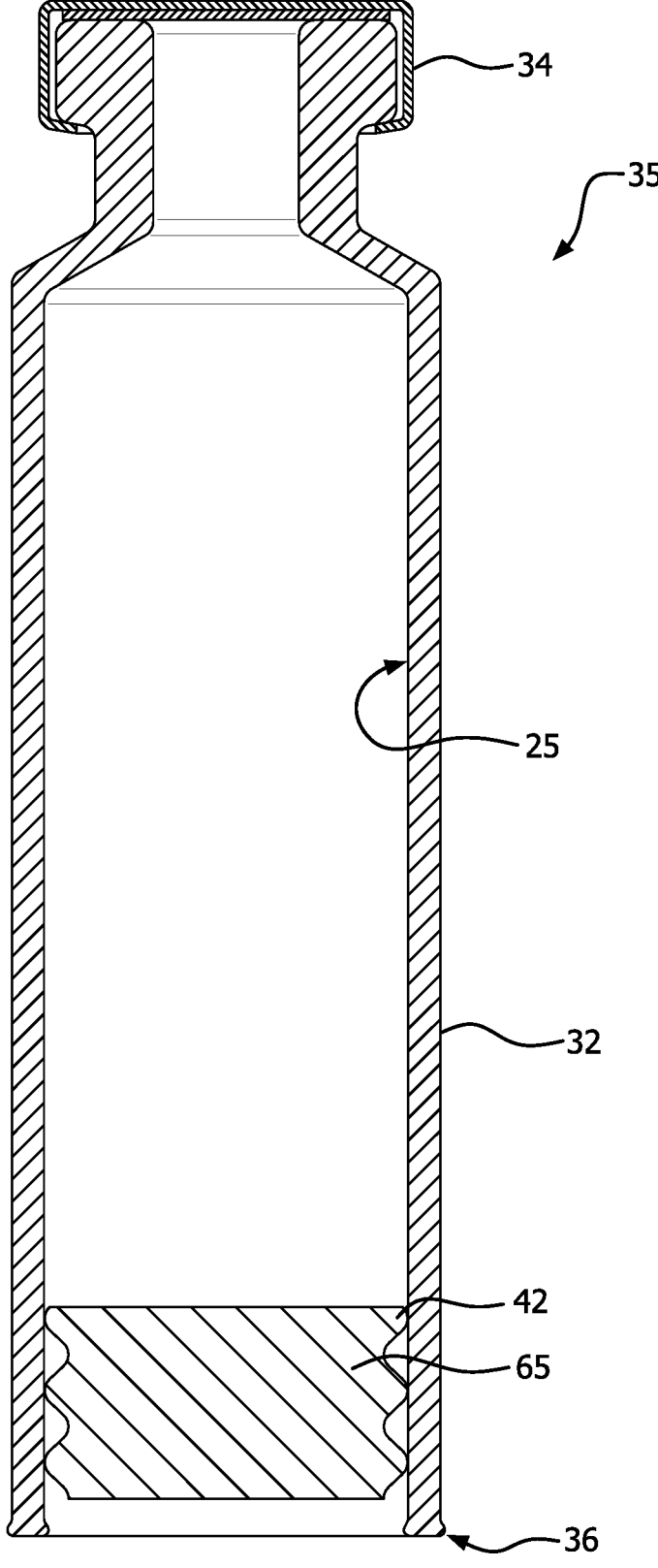
FIG. 1B is a schematic illustration of a cartridge in accordance with some embodiments.

Turning to FIG. 1B, in a cartridge 35, the plunger rod (not shown) and the stopper 65 are not attached. It is to be noted that stopper 65 has no cavity therein. The stopper 65 contacts at least a portion of the inner surface 25 of the cartridge tube 32 via one or more ribs, such as sealing rib 42. The cartridge 35 contains a stopper 65, a sealed cap 34, a cartridge tube 32, and a sealing end portion 36. It is to be appreciated that the components of the syringe 10 and the cartridge 35 are lubricant free or substantially lubricant free as described in detail below.

Figure 2:
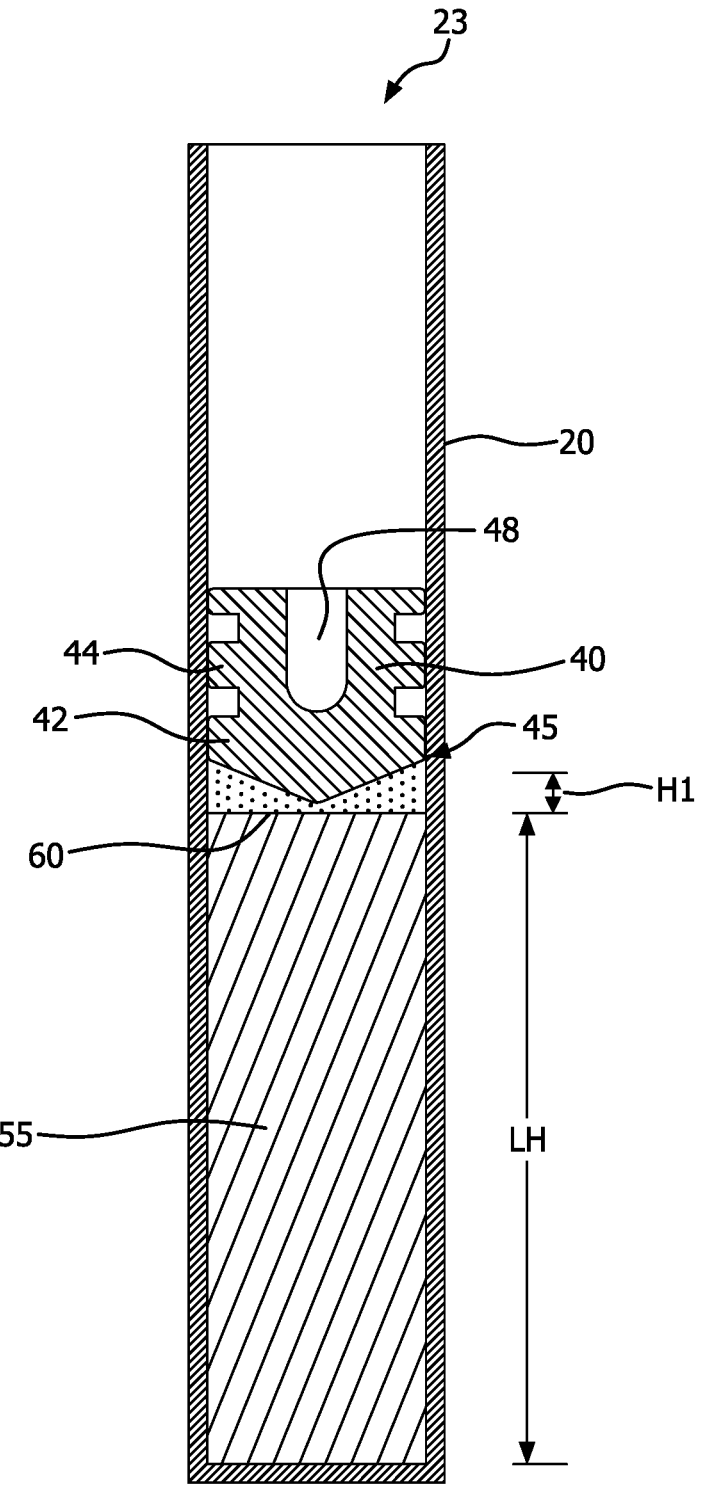
FIG. 2 is a schematic illustration depicting the head space between a stopper and the liquid in a barrel or cartridge tube in accordance with some embodiments.

Turning to FIG. 2, in some syringe barrels, the stopper 40 is inserted into the proximal end 23 of the barrel 20 and is translated through the barrel 20 until it reaches a specific, desired location within the barrel 20. As shown, the stopper 40 contains an internal cavity 48 therein. It is to be appreciated that the phrase "barrel 20" may be equally interchanged with the phrase "cartridge tube 32" herein. The desired location is a predetermined height above the liquid surface 60 of a therapeutic solution 55 in the barrel 20. The therapeutic solution 55 can have a liquid height LH. LH is a function of the amount of therapeutic solution 55 located within the barrel 20, which, in turn, depends on the volume of the therapeutic substance that is to be administered. In some embodiments, the location of the stopper 40 within the barrel 20 allows for a specific amount of headspace H1. As used herein, "headspace" is meant to describe the height (distance) from the top of the liquid surface 60 to the front edge 45 of the front sealing rib 42 of the stopper 40. Sealing rib 44 is shown for illustrative purposes only. In some embodiments, the headspace H1 is minimized to reduce the amount of air in the barrel 20 that might be injected into a patient, for drug stability, and/or for shipping purposes.

In some embodiments, after insertion of the stopper 40 using one of the methods described herein, the headspace H1 (i.e., height or distance) is less than about 25 mm, less than about 23 mm, less than about 21 mm, less than about 19 mm, less than about 17 mm, less than about 15 mm, less than about 13 mm, less than about 10 mm, less than about 8 mm, less than about 5 mm, less than about 3 mm, less than about 2 mm, less than about 1 mm, or less than about 0.5 mm. In some embodiments, the headspace H1 may range from about 1 mm to about 25 mm, from about 1 mm to about 23 mm, from about 1 mm to about 21 mm, from about 1 mm to about 19 mm, from about 1 mm to about 17 mm, from about 1 mm to about 15 mm, from about 1 mm to about 13 mm, from about 1 mm to about 10 mm, from about 1 mm to about 8 mm, from about 1 mm to about 5 mm, from about 1 mm to about 3 mm, from about 1 mm to about 2 mm, from about 0.5 mm to about 2 mm, or from about 0.5 mm to about 1 mm.

The barrel 20 and cartridge tube 32 may be formed of a hard material, such as a glass material (e.g., borosilicate glass), a ceramic material, one or more polymeric materials (e.g., polypropylene, polyethylene, and copolymers thereof), a metallic material, a plastic material (e.g., cyclic olefin polymers and cyclic olefin copolymers), and combinations thereof. In certain embodiments, the barrel 20 or cartridge tube 32 may be formed of glass, resin, plastic, or metal without any lubricants (e.g., silicone) present on the inner surface 25 of the barrel 20 or cartridge tube 32.

Figure 3:
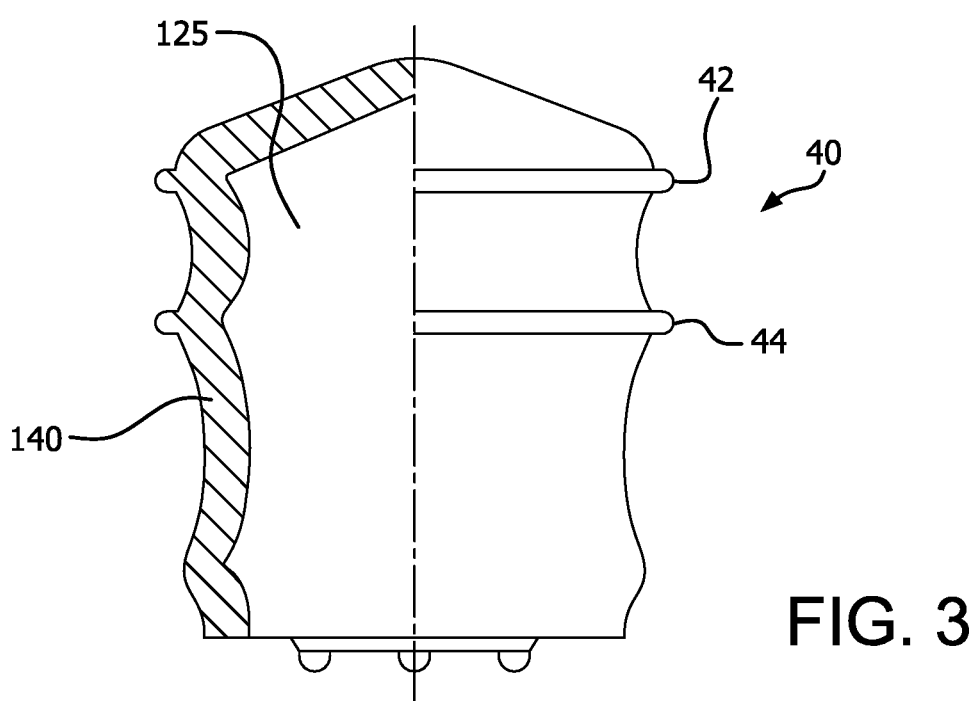
FIG. 3 is a schematic illustration of a cutaway view of a stopper having thereon a polymer layer in accordance with some embodiments.
Figure 4:
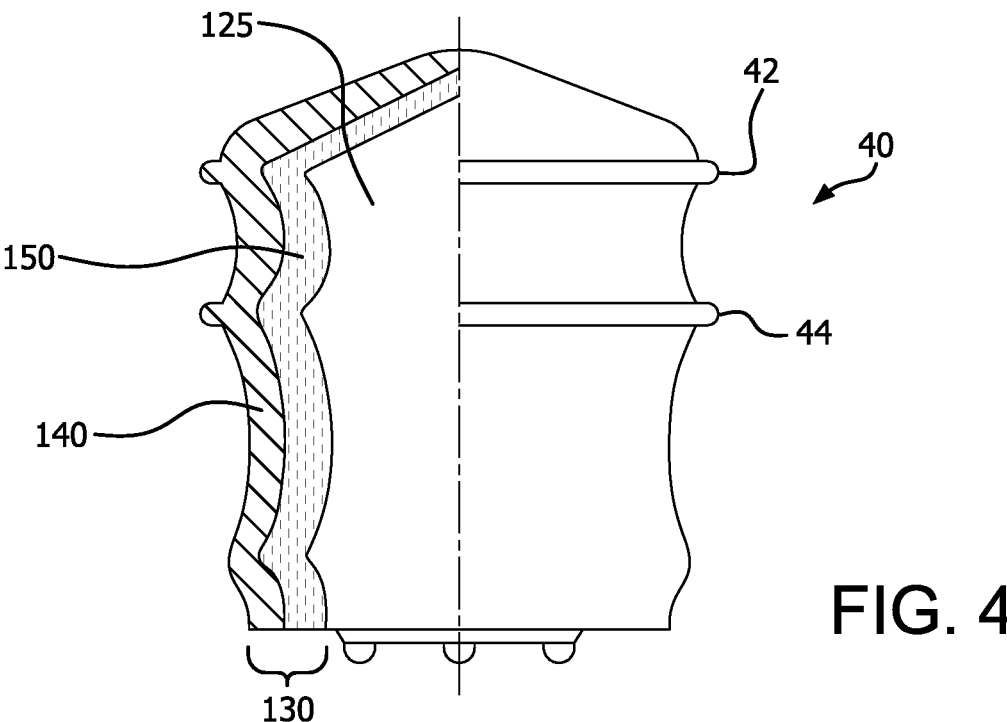
FIG. 4 is a schematic illustration of a cutaway view of a stopper having thereon a laminate in accordance with some embodiments.

The stopper 40 may be formed of an elastomeric body at least partially covered by a polymer (e.g., an expanded polymer). In some embodiments, the elastomeric body may have thereon one or more polymer or expanded polymer layers (e.g., polymer membrane(s)). It is to be appreciated that the terms "membrane" and "layer" may be interchangeably used herein. FIG. 3 illustrates a stopper 40 that has an elastomeric body 125 and a single layer of a polymer or expanded polymer 140 at least partially covering the elastomeric body 125. In another embodiment depicted in FIG. 4, the stopper 40 includes an elastomeric body 125 and a laminate layer 130 that may be formed of a polymer or expanded polymer 140 (e.g. an expanded fluoropolymer) and a porous layer 150 (e.g., fluorinated ethylene propylene (FEP)). As discussed above, the stopper 40 may have one or more sealing ribs, such as sealing ribs 42, 44, extending therefrom.

In some embodiments, the expanded polymer is an expanded fluoropolymer. Examples of fluoropolymers that may be utilized as a polymer or expanded polymer layer 140 or as the porous layer 150 include, but are not limited to, polytetrafluoroethylene (PTFE), expanded polytetrafluoroethylene (ePTFE), densified expanded polytetrafluoroethylene (ePTFE), densified polytetrafluoroethylene (PTFE), modified PTFE, expanded modified PTFE, expanded copolymers of PTFE, ethylene-(perfluoro-ethylene-propene) copolymer (EFEP), polyvinylidene difluoride (PVDF), fluorinated ethylene propylene (FEP), perfluoroalkoxy copolymer resin (PFA), polyvinylfluoride, perfluoropropylevinylether, and perfluoroalkoxy polymers. Patents have been granted on expandable blends of PTFE, expandable modified PTFE, and expandable copolymers of PTFE, such as, but not limited to, U.S. Pat. No. 5,708,044 to Branca; U.S. Pat. No. 6,541,589 to Baillie; U.S. Pat. No. 7,531,611 to Sabol et al.; U.S. Pat. No. 8,637,144 to Ford; and U.S. Pat. No. 9,139,669 to Xu et al. Non-fluoropolymers such as polyethylene, polypropylene, and polycarbonate may also be utilized as a polymer or expanded polymer layer 140.

Non-limiting examples of elastomers that can be used to form the elastomeric body 125 include any elastomer suitable for the application, most notably rubbers constructed from butyl, bromobutyl, chlorobutyl, silicone, nitrile, styrene butadiene, polychloroprene, ethylene propylene diene, fluoroelastomers, thermoplastic elastomers (TPE), thermoplastic vulcanizates (TPV), and combinations and blends thereof. In some embodiments, the elastomeric body 125 may have an initial modulus ranging from about 2.5 MPa to about 5 MPa. In some embodiments, the elastomeric body 125 may have an initial modulus from about 3 MPa to about 4 MPa. In one non-limiting embodiment, the initial modulus may be, for example, about 3.5 MPa.

The laminate layer 130 may have a thicknesses less than about 30 microns. In some embodiments, the thickness of the laminate layer 130 may range from about 0.5 microns to about 20 microns. The membrane forming the polymer or expanded polymer layer 140 (FIG. 3) and/or the porous layer 150 (FIG. 4) may be pre-treated or post-treated with chemical etching, plasma treating, corona treatment, roughening, or the like to improve the bonding of the polymer or expanded polymer layer 140 and/or the porous layer 150 to the elastomeric body 125. The materials of the laminate layer 130 and polymer or expanded polymer layer 140 are chosen to provide a low coefficient of friction, compliance, low extractables and leachables, and good barrier properties as they relate to extractables and leachables from the elastomeric body 125, as well as good air and liquid impermeability.

In another embodiment, the polymer or expanded polymer layer 140 may be used with non-elastomeric materials such as, but not limited to plastics (e.g., polypropylene, polycarbonate, and polyethylene), thermoplastics, and fluoropolymer materials such ethylene-(perfluoro-ethylene-propene) copolymer (EFEP), polyvinylidene difluoride (PVDF), and perfluoroalkoxy polymer resin (PFA).

Figure 5B:
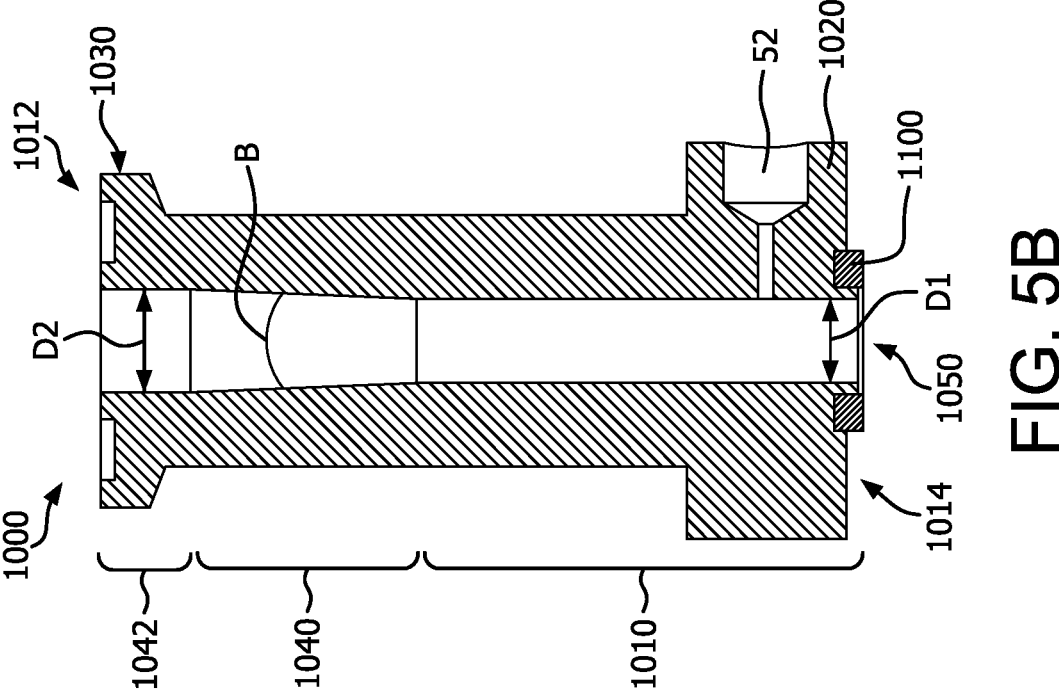
FIG. 5B is a cross-sectional view of the vacuum chamber of FIG. 5A.
Figure 5A:
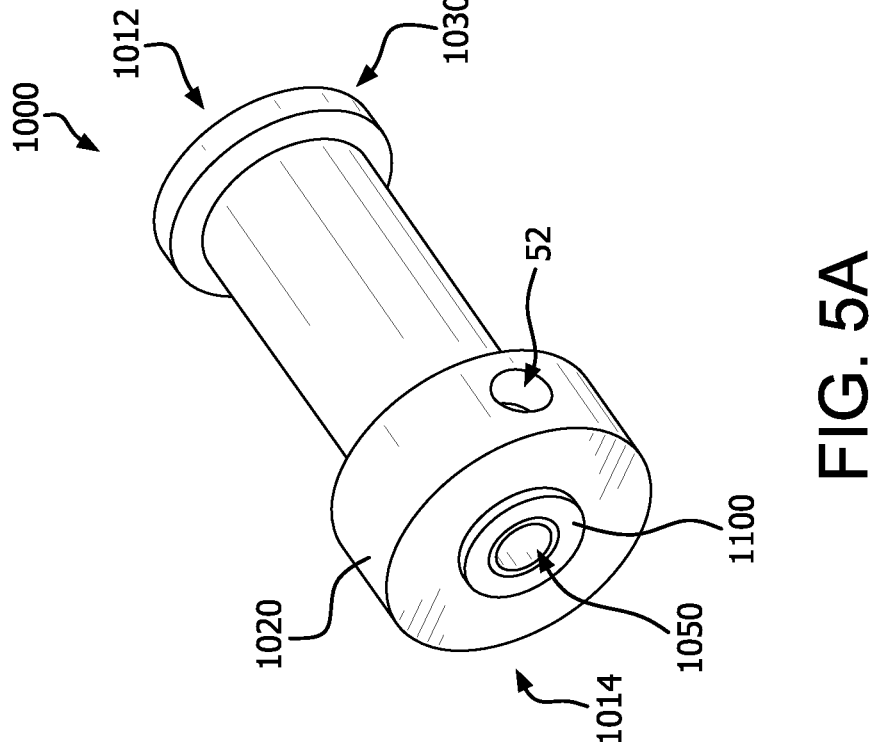
FIG. 5A is an isometric view of a vacuum chamber according to some embodiments.

In some embodiments, a vacuum chamber and an insertion pin may be used in combination to insert a lubricant free stopper into a non-lubricated syringe barrel 20 or non-lubricated cartridge tube 32 with little to no distortion, buckling, or wrinkling of the stopper. Turning now to FIGS. 5A and 5B, an exemplary vacuum chamber 1000 is shown. The vacuum chamber 1000 allows a non-lubricated stopper to be placed inside a non-lubricated syringe barrel or non-lubricated cartridge tube without over-pressurizing the liquid (e.g., therapeutic solution) contained therein. As shown in FIGS. 5A and 5B, the vacuum chamber 1000 has a proximal end 1012 and a distal end 1014. The vacuum chamber 1000 also includes an insertion tube 1010 and a machine adaptor 1020. An alignment flange 1030 protrudes from the proximal end 1012 of the vacuum chamber 1000. The alignment flange 1030 and machine adapter 1020 have a shape that is sufficient to align with auxiliary equipment on a conventional syringe filling line (not depicted). The insertion tube 1010 is the portion of the vacuum chamber 1000 that holds and guides the non-lubricated stopper into a non-lubricated syringe barrel or non-lubricated cartridge tube. The inner diameter D1 (FIG. 5B) of the insertion tube 1010 is sized to either match or to be smaller than the inner diameter of the syringe barrel or cartridge tube into which it is to be inserted such that the non-lubricated stopper can translate from the insertion tube 1010 into the syringe barrel. The vacuum chamber 1000 also includes a vacuum port 52 which allows a vacuum to be drawn within the headspace once the vacuum chamber 1000 is sealably connected to the syringe barrel 20 or cartridge tube 32. The vacuum chamber 1000 is sealably connected to the syringe barrel 20 or cartridge tube 32 when the gasket 1100 is compressed against the barrel flange 70 or sealing end portion 36 of the cartridge tube.

The transition zone 1040 is a portion of the vacuum chamber 1000 where the stopper is compressed to a diameter D1 that is sufficient to pass through the distal opening 1050 of the insertion tube 1010. Thus, the diameter of the stopper (not shown) is reduced from D2 (i.e., the diameter of the placement region 1042) to D1 (i.e., the diameter at the distal opening 1050 of the insertion tube 1010). The transition zone 1040 tapers from the placement region 1042 to the insertion tube 1010 at a taper angle (B). The placement region 1042 has a diameter D2 from about 3 mm to about 20 mm, about 5 mm to about 15 mm, from about 7 mm to about 10 mm, from about 7 mm to about 8 mm, or from about 7.5 mm to about 8 mm. The taper angle (B) may range from about 0.1 degree to about 20 degrees, from about 0.05 degree to about 20 degrees, from about 1 degree to about 20 degrees, from about 3 degrees to about 20 degrees, from about 5 degrees to about 20 degrees, or from about 0.01 degree to about 15 degrees, from about 0.05 degree to about 15 degrees, from about 1 degree to about 15 degrees, from about 2 degrees to about 15 degrees, from about 3 degrees to about 15 degrees, from about 4 degrees to about 15 degrees, from about 5 degrees to about 15 degrees, from about 1 degree to 10 degrees, or from about 5 degrees to about 10 degrees.

Figure 6B:
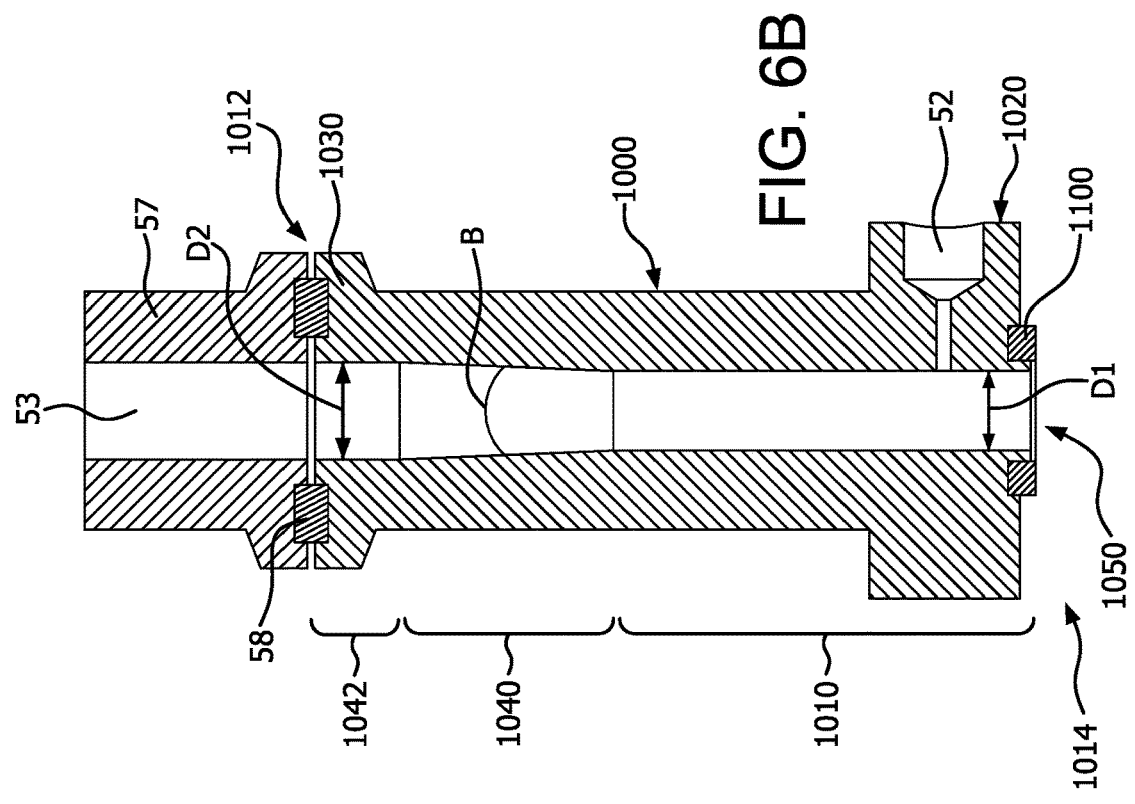
FIG. 6B is a cross-sectional view of the vacuum chamber of FIG. 6A in accordance with some embodiments.
Figure 6A:
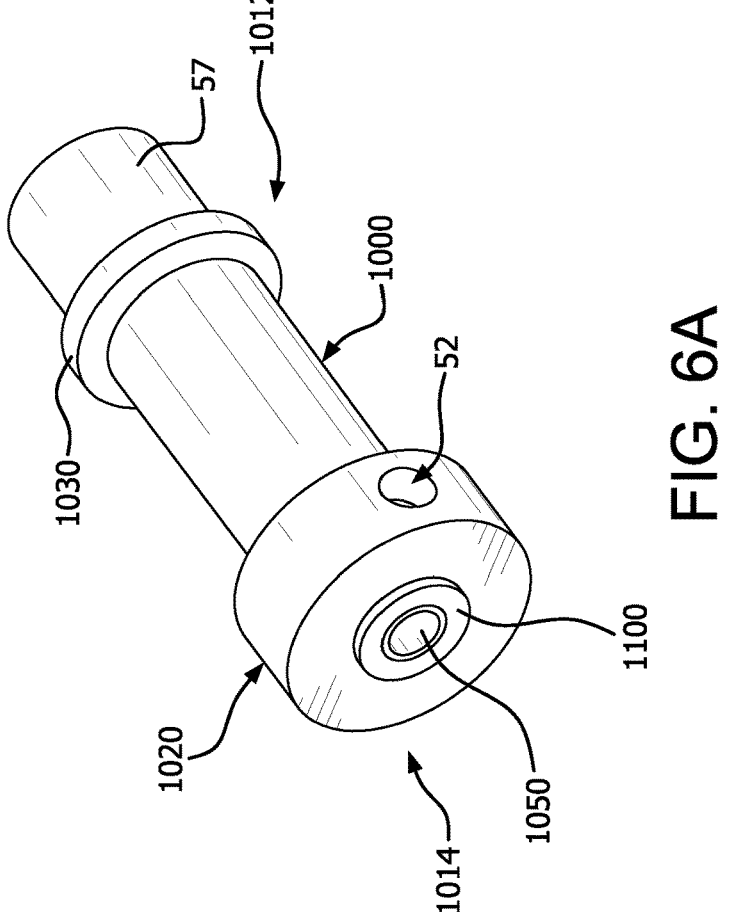
FIG. 6A is an isometric view of a vacuum chamber of FIG. 5A having thereon a pressure sealing cap according to some embodiments.

FIGS. 6A and 6B depict a vacuum chamber 1000 with a pressure sealing cap 57 attached thereto. The pressure sealing cap 57 includes a pressure port 53 which allows pressure to be applied to the distal end of the stopper 40 once the vacuum chamber 1000 with the pressure sealing cap 57 is sealably connected to the syringe barrel 20 or cartridge tube 32. The vacuum chamber 1000 with the pressure sealing cap 57 is sealably connected to the syringe barrel 20 or cartridge tube 32 when the gasket 1100 of the vacuum chamber 1000 is compressed against the barrel flange 70 or sealing end portion 36 of the cartridge tube, and when the pressure sealing cap gasket 58 is compressed against the alignment flange 1030 of the vacuum chamber 1000, as discussed in detail below.

Figure 7A:
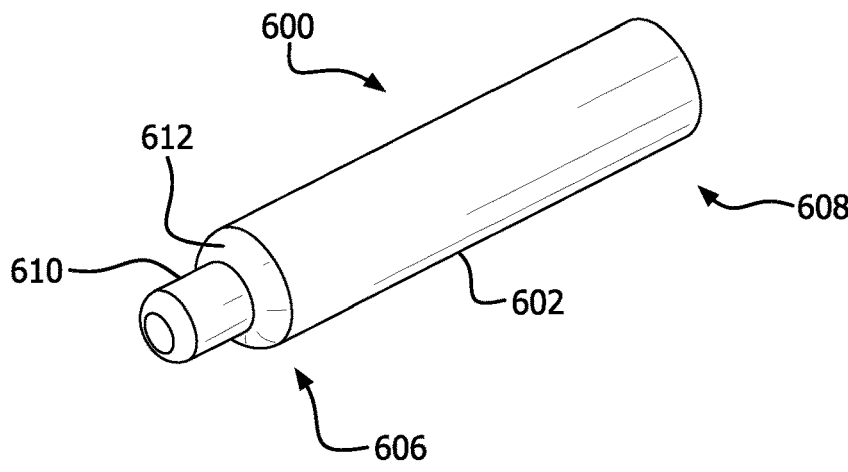
FIG. 7A is an isometric view of an insertion pin in accordance with some embodiments.
Figure 7B:
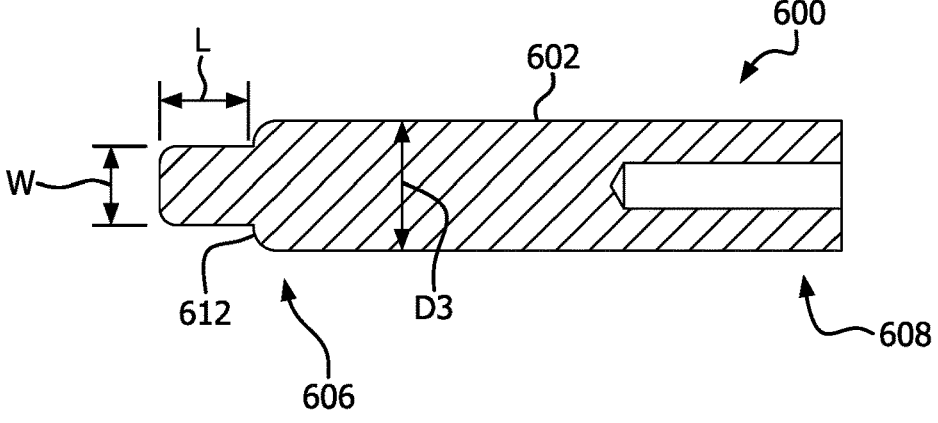
FIG. 7B is a cross-sectional view of the insertion pin of FIG. 7A.
Figure 7C:
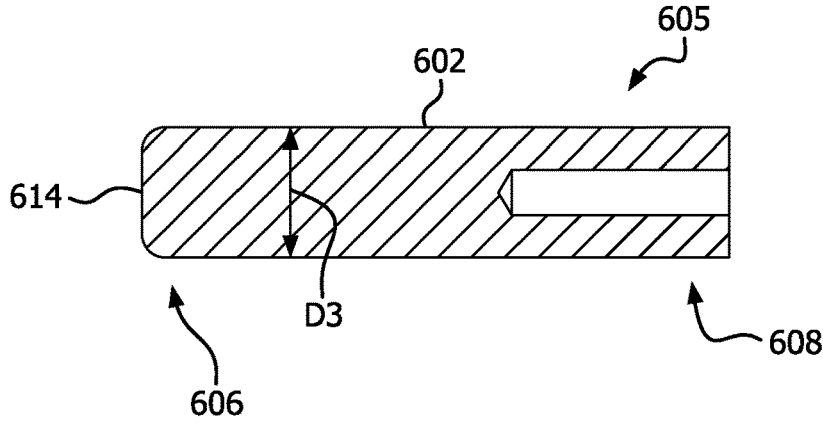
FIG. 7C is a cross-sectional view of another insertion pin in accordance with some embodiments.

FIGS. 7A, 7B, and 7C illustrate an insertion pin 600 (FIGS. 7A and B) and an insertion pin 605 (FIG. 7C) that may be used in combination with a vacuum chamber, such as the vacuum chamber 1000 illustrated in FIGS. 5A and 5B, to insert a non-lubricated stopper into a non-lubricated barrel or non-lubricated cartridge tube. The insertion pins 600 and 605 include a cylindrical body 602 having a proximal end 606 and a distal end 608. The pin tip end 610 of insertion pin 600 is connected to the cylindrical body 602 and interfaces with the cavity of a stopper (not shown). The distal end 608 may be sized to mate with a machine adapter (not shown) used to push the insertion pin 600 and insertion pin 605 through a vacuum chamber, such as the vacuum chamber 1000 shown in FIGS. 5A and 5B.

The cylindrical body 602 has a diameter D3 that is slightly smaller than the inner diameter D1 of the insertion tube in a vacuum chamber (e.g., diameter D1 of the insertion tube 1010 depicted in FIGS. 5A and 5B). The radiused surface 612 of the cylindrical body 602 is designed to push against the distal end of a stopper to provide straightness and stability during the insertion of the stopper into the non-lubricated syringe barrel. The cylindrical body 602 has a diameter D3 that may range from about 2 mm to about 18 mm, including any and all subranges therebetween. In other embodiments, the radiused surface 612 may include or be formed of shapes other than a radius, such as, for example, a flat section, a straight taper (e.g. linear), curvilinear, rounded, or have multiple tapers. In at least one embodiment, a stopper without an internal cavity may be used and the insertion pin may be modified to reduce or even eliminate the pin tip end, such as is depicted in FIG. 7C. As shown in FIG. 7C, the insertion pin 605 is devoid of a pin tip end and instead is formed of a flat or substantially flat surface 614.

Turning back to FIG. 7A and FIG. 7B, the pin tip end 610 has a length (L) that may be approximately the depth of the inner cavity of a stopper. In some embodiments, the pin tip end 610 has a length from about 3 mm to about 8 mm, from about 4 mm to about 7 mm, from about 4.5 mm to about 5.5 mm, or from about 5 mm to about 6 mm. In addition, the pin tip end 610 may have a width (W) that may be approximately the width of the inner cavity of a stopper. In some embodiments, the pin tip end 610 has a width from about 0.5 mm to about 5 mm, from about 1 mm to about 4 mm, from about 1 mm to about 3 mm, from about 2 mm to about 3 mm, from about 1.5 mm to about 2.5 mm, from about 3 mm to about 6 mm, from about 5 mm to about 9 mm, or from 8 mm to about 11 mm. The combination of the width (W) and length (L) of the pin tip end 610 creates a volume that is compatible with the cavity of the stopper during insertion. In the embodiment depicted in FIGS. 7A and 7B, the tip end 610 has a rounded end. The stopper 40 may be inserted into the vacuum chamber 1000 at a peak insertion force that ranges from about 10 N to about 200 N, from about 20 N to about 100 N, from about 30 N to about 80 N, from about 40 N to about 60 N, or from about 40 N to about 60 N. In some embodiments, the peak insertion force is greater than zero and less than about 50 N, greater than zero and less than about 40 N, greater than zero and less than about 30 N, or greater than zero and less than about 20 N.

The insertion pins 600, 605 may be formed from a polymeric material such as polyether ether ketone (PEEK), polytetrafluoroethylene (PTFE), expanded polytetrafluoro-ethylene (ePTFE), or metallic materials such as stainless steel or a combination thereof.

Figures 8A, 8B, 8C, 8D, 8E:
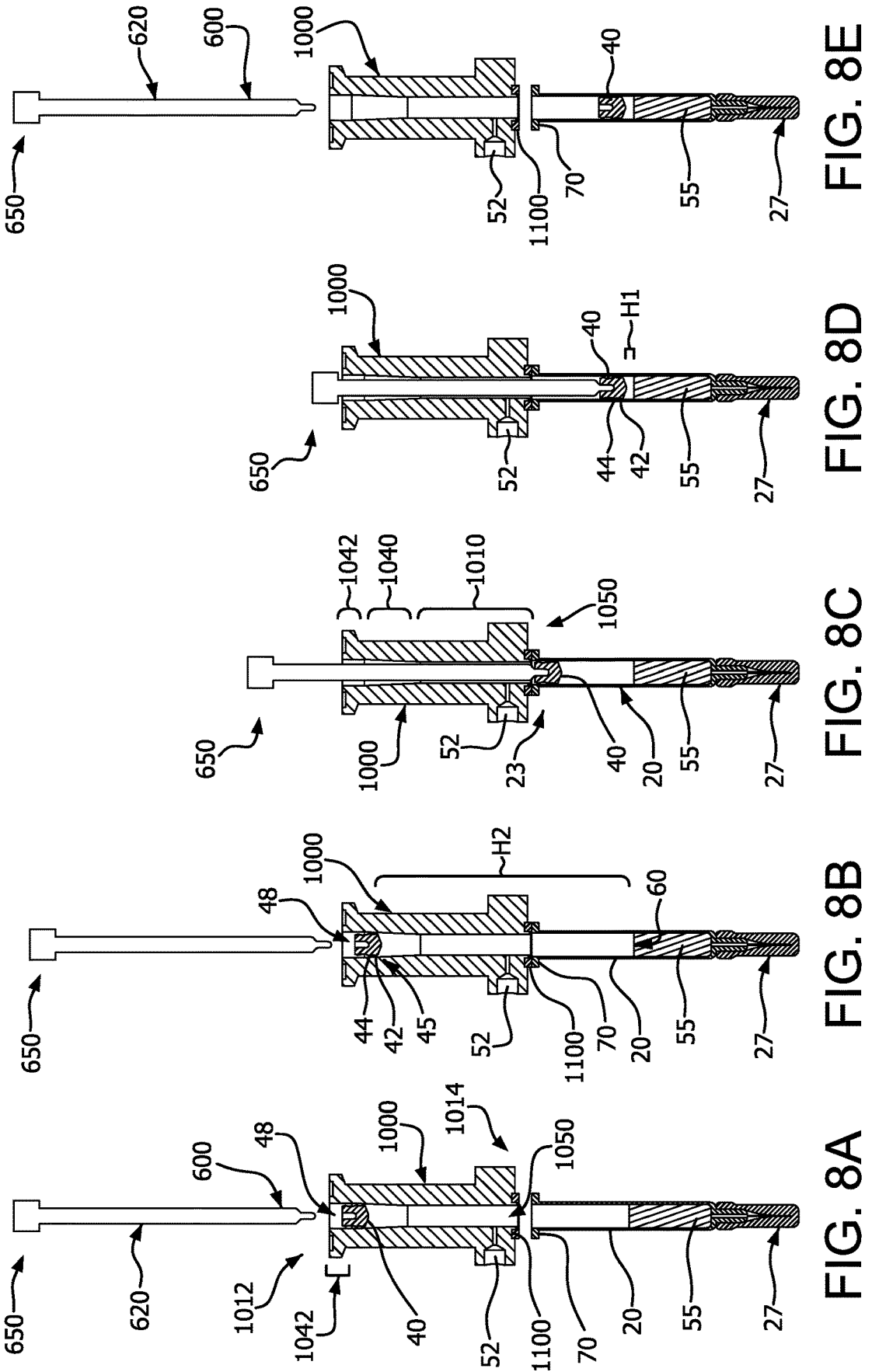
FIGS. 8A-8E depict a vacuum insertion method for a non-lubricated syringe barrel that utilizes a vacuum chamber in conjunction with an insertion pin in accordance with some embodiments.
Figures 10A, 10B, 10C, 10D, 10E:
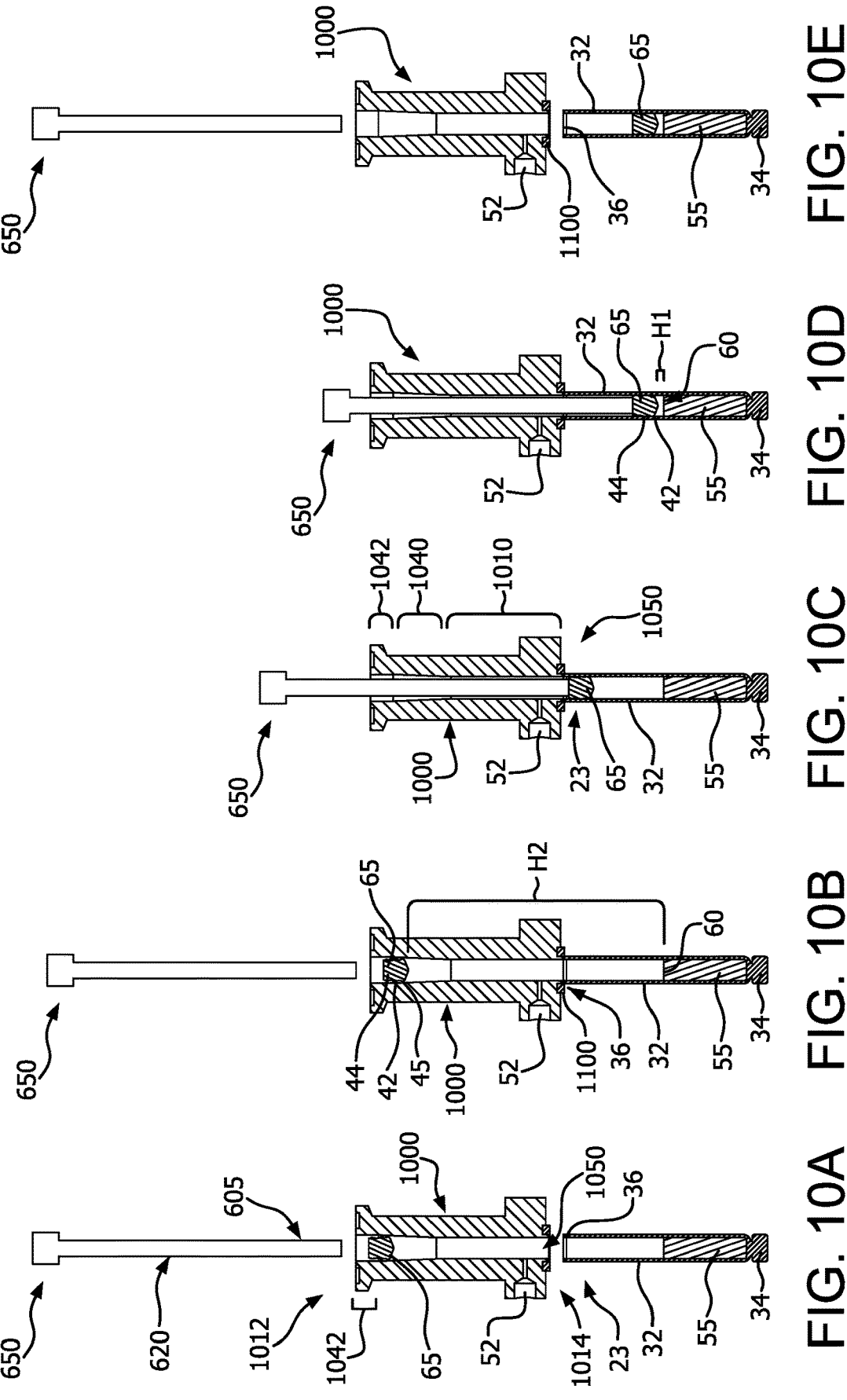
FIGS. 10A-10E depict a vacuum insertion method for a non-lubricated cartridge tube that utilizes a vacuum chamber in conjunction with an insertion pin in accordance with some embodiments.

Turning now to FIGS. 8A-8E and FIGS. 10A-10E, a cross section of a vacuum method for the insertion of a non-lubricated stopper at least partially covered with a polymer or expanded polymer layer or laminate layer into a non-lubricated syringe barrel (FIGS. 8A-8E) and into a non-lubricated cartridge tube (FIGS. 10A-10E) is depicted in a series of steps. It is to be noted that the tip cap 27 attached to the barrel 20 is shown in FIGS. 8A-8E for illustrative purposes only. In FIGS. 8A-8E and FIGS. 10A-10E, an insertion rod 650 that includes either an insertion pin 600 (FIG. 8A-8E) or an insertion pin 605 (FIGS. 10A-10E) and a machine adapter 620 is shown. Initially, as shown in FIG. 8A, a stopper 40 having an internal cavity 48 is placed into the placement region 1042 located at the proximal end 1012 of the vacuum chamber 1000. The distal end of the vacuum chamber 1000 is indicated generally by reference numeral 1014. The vacuum chamber 1000 is positioned above and aligned with the syringe barrel 20. In some embodiments, the syringe barrel 20 has already been filled with a thera-peutic solution 55. In FIG. 10A, a solid stopper 65 (i.e., without a cavity therein) is placed into the placement region 1042 located at the proximal end 1012 of the vacuum chamber 1000. The insertion rod 650 has a flat or substan-tially flat end as shown in FIG. 7C. Although not depicted, it is to be appreciated that a stopper 40 (with a cavity therein) may be used in place of the solid stopper 65 in the cartridge tube 32. In such an embodiment, the insertion rod 650 would have a pin tip end as shown in FIGS. 7A, 7B. The distal end of the vacuum chamber 1000 is indicated generally by reference numeral 1014. The vacuum chamber 1000 is positioned above and is aligned with the cartridge tube 32. In some embodiments, the cartridge tube 32 has already been filled with a therapeutic solution 55.

Looking at FIG. 8B, the vacuum chamber 1000 is lowered so that the sealing gasket 1100 of the vacuum chamber 1000 creates a vacuum seal on the barrel flange 70 of the syringe barrel 20. Similarly, as shown in FIG. 10B, the vacuum chamber 1000 is lowered so that the sealing gasket 1100 creates a vacuum seal on the sealing end portion 36 of the cartridge tube 32. In both FIG. 8B and FIG. 10B, vacuum is applied to the headspace H2 between the top of the liquid surface 60 and the front edge 45 of the front sealing rib 42 of stopper 40, 65 via a vacuum port 52. The amount of vacuum that is applied is dependent on the therapeutic substance 55 and its sensitivity to vacuum, which would easily be determined by one of skill in the art.

The stopper 40, 65 is translated through the vacuum chamber 1000 via the insertion rod 650, from the placement region 1042 through the transition zone 1040 and through the length of the insertion tube 1010 until it exits the distal opening 1050 of the vacuum chamber 1000 and into the proximal end 23 of the syringe barrel 20 or cartridge tube 32, as depicted in FIGS. 8C and 10C. The stopper 40, 65 is further translated by an insertion rod 650 that includes an insertion pin 600 (FIG. 8C) or an insertion pin 605 (FIG. 10C).

As shown in FIG. 8D and FIG. 10D, the stopper 40, 65 is translated by the insertion rod 650 down the length of the syringe barrel 20 or cartridge tube 32, decreasing the head-space H2 until the final desired headspace H1 is achieved. In some embodiments, after the stopper 40, 65 has been placed in its final position, the insertion rod 650 is retracted from the stopper 40, 65 and the vacuum chamber 1000. The vacuum chamber 1000 may, either sequentially or simulta-neously, be retracted so that the sealing gasket 1100 is removed from barrel flange 70 or end portion 36 of the cartridge tube 32, shown in FIGS. 8E and 10E.

Figure 9C:
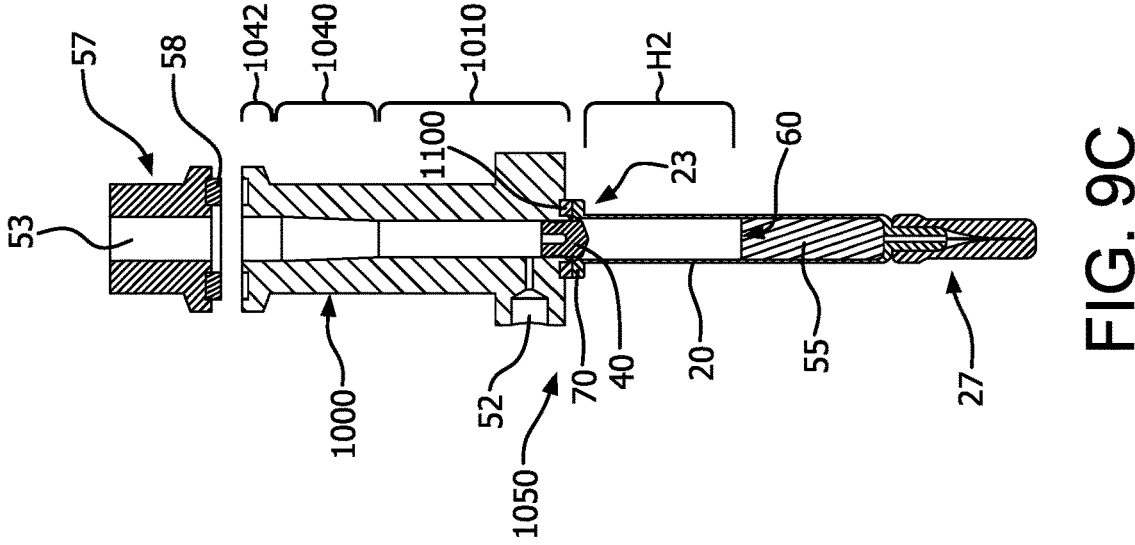
FIGS. 9A-9F depict a vacuum insertion method for a non-lubricated syringe barrel that utilizes a vacuum chamber with a pressure sealing cap in accordance with some embodiments.
Figure 9B:
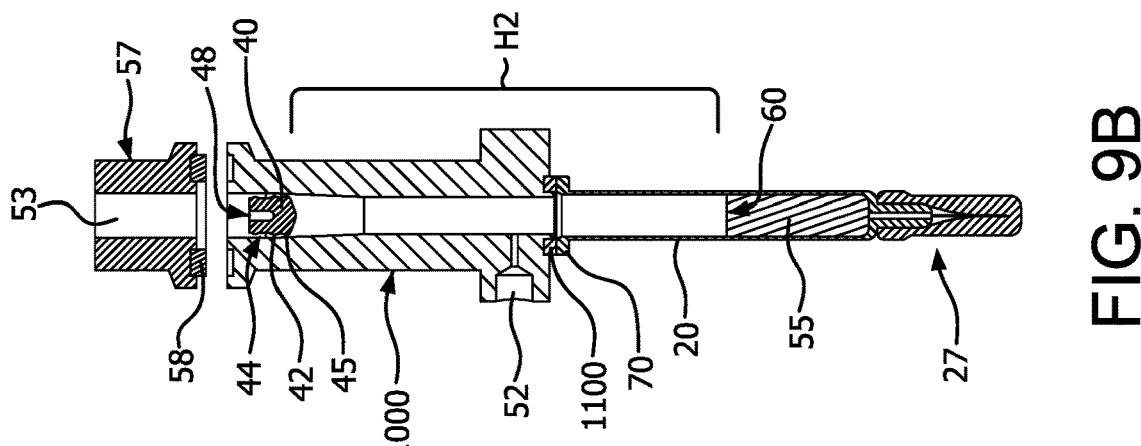
Figure 9A:
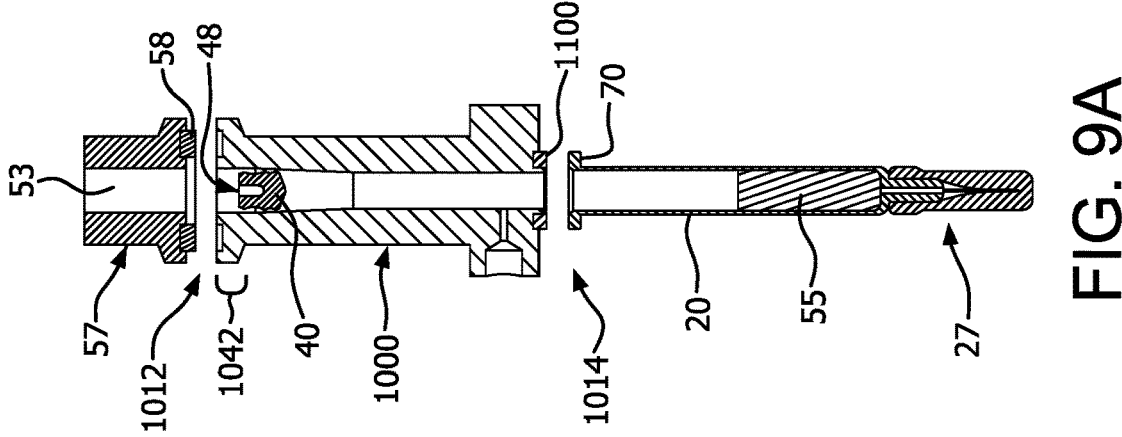
Figure 11C:
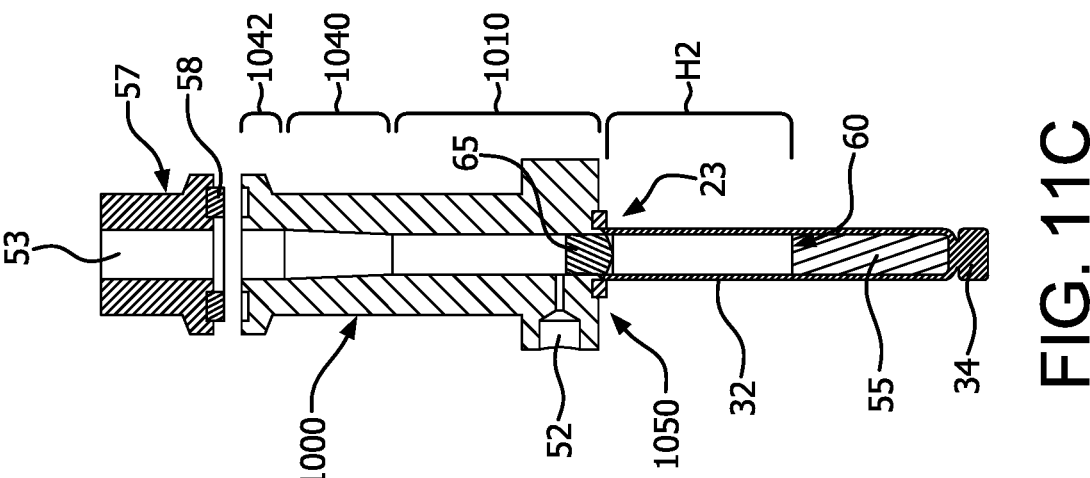
FIGS. 11A-11F depict a vacuum insertion method for a non-lubricated cartridge tube that utilizes a vacuum chamber with a pressure sealing cap in accordance with some embodiments.
Figure 11B:
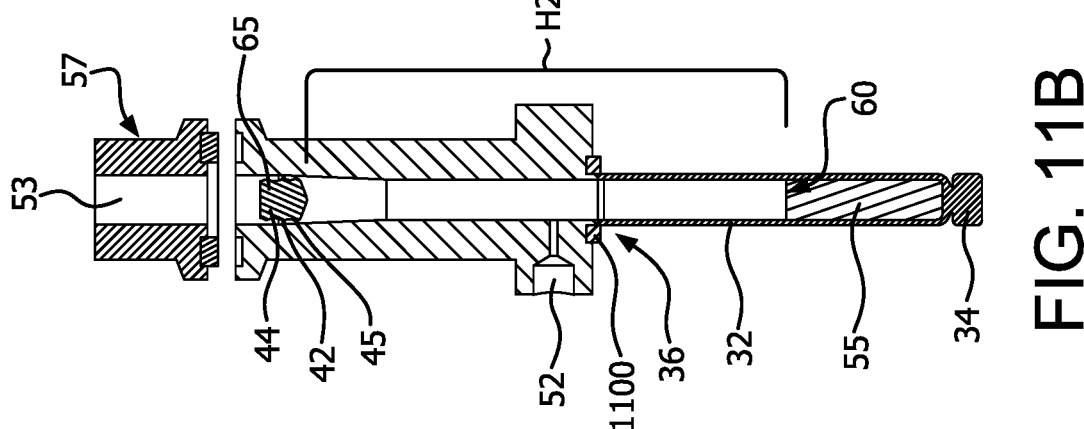
Figure 11A:
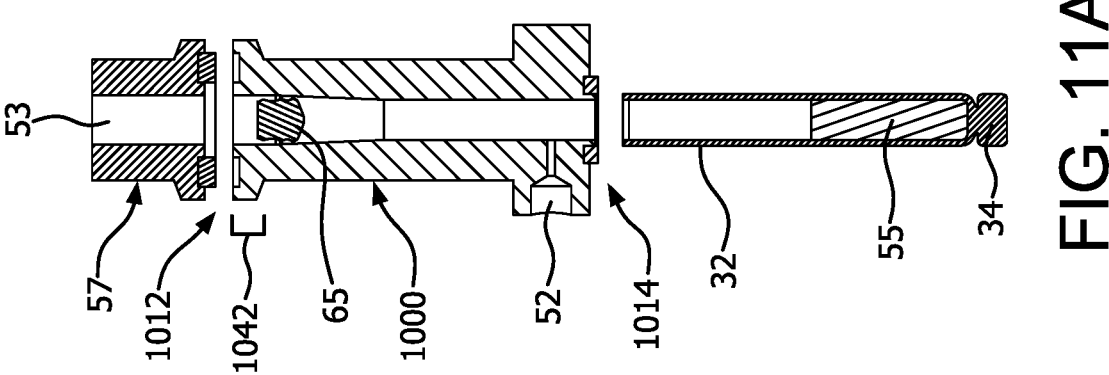

Turning now to FIGS. 9A-9F and FIGS. 11A-11F, embodiments of methods for the insertion of a non-lubri-cated stopper at least partially covered with a polymer or expanded polymer layer or laminate layer into a non-lubricated syringe barrel (FIGS. 9A-9F) or into a non-lubricated cartridge tube (FIGS. 11A-11F) utilizing a vacuum chamber 1000 in combination with a pressure sealing cap 57 (such as is illustrated in FIG. 6A and FIG. 6B) is depicted in a series of steps. It is to be noted that the tip cap 27 attached to the barrel 20 is shown in FIGS. 9A-9F for illustrative purposes only. Initially, as shown in FIG. 9A, a stopper 40 having a cavity 48 is placed into the placement region 1042 located at the proximal end 1012 of the vacuum chamber 1000. The distal end of the vacuum chamber is indicated generally by reference numeral 1014. A pressure sealing cap 57 is positioned above and is aligned with the syringe barrel 20. In some embodiments, the syringe barrel 20 has already been filled with a therapeutic solution 55. Turning to FIG. 11A and the insertion of a non-lubricated stopper into a non-lubricated cartridge tube, a solid stopper 65 (i.e., without a cavity therein) is placed into the place-ment region 1042 located at the proximal end 1012 of the vacuum chamber 1000 having a distal end indicated gener-ally by reference numeral 1014. A pressure sealing cap 57 is positioned above and is in alignment with the cartridge tube 32. In some embodiments, the cartridge tube 32 has already been filled with a therapeutic solution 55.

Looking at FIG. 9B, the vacuum chamber 1000 is lowered so that the sealing gasket 1100 of the vacuum chamber 1000 creates a vacuum seal on the barrel flange 70 of the syringe barrel 20. Similarly, as shown in FIG. 11B, the vacuum chamber 1000 is lowered so that the sealing gasket 1100 creates a vacuum seal on the sealing end portion 36 of the cartridge tube 32. In both FIG. 9B and FIG. 11B, vacuum is applied to the headspace H2 between the top of the liquid surface 60 and the front edge 45 of the front sealing rib 42 of stopper 40, 65 via a vacuum port 52. The amount of vacuum that is applied is dependent on the therapeutic substance 55 and its sensitivity to vacuum, which would be easily determined by one of skill in the art.

Figure 9F:
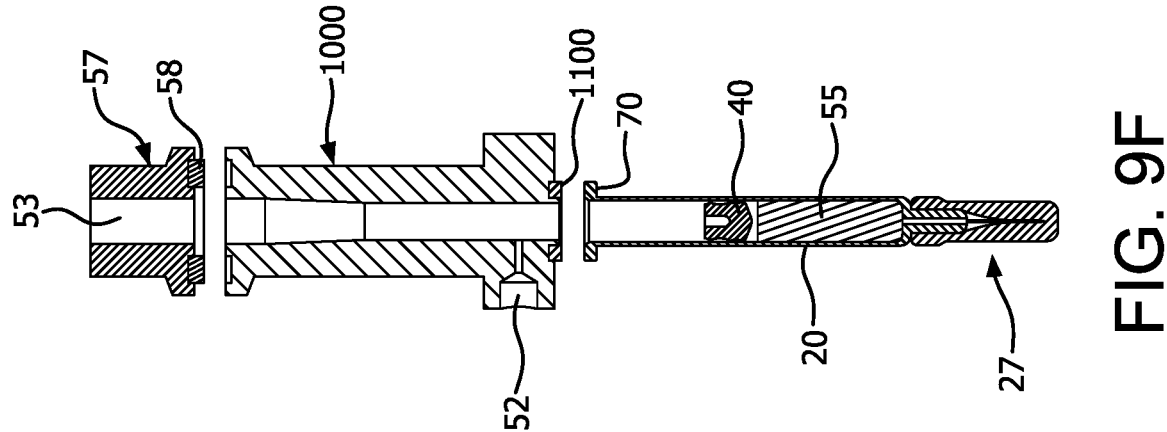
Figure 11F:
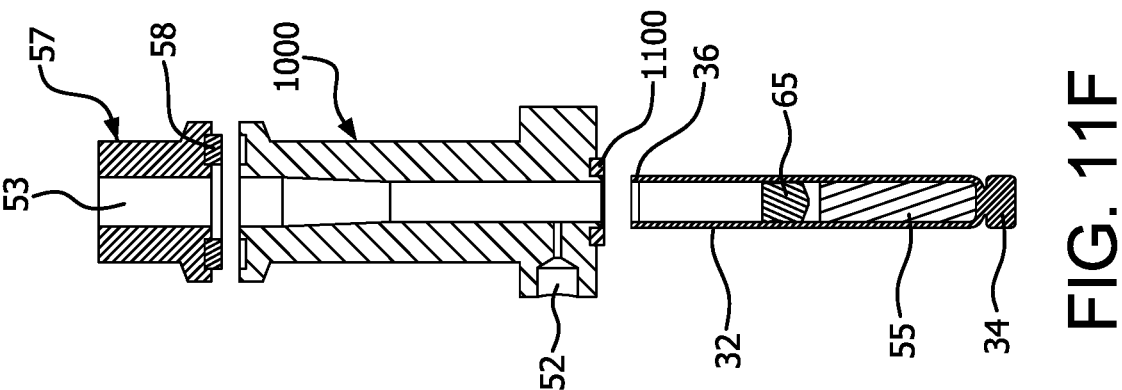

As shown in FIG. 9C and FIG. 11C, the stopper 40, 65 is translated through the vacuum chamber 1000 from the placement region 1042 through the transition zone 1040 and through the length of the insertion tube 1010 until it exits the distal opening 1050 of the vacuum chamber 1000 and into the proximal end 23 of the syringe barrel 20 or cartridge tube 32. The stopper 40, 65 is translated by differential pressure created by the vacuum in the headspace H2 (created in the step depicted in FIGS. 9B and 11B). Next, the pressure sealing cap 57 is lowered so that the pressure sealing cap gasket 58 of the pressure sealing cap 57 creates a seal with the vacuum chamber 1000, as depicted in FIGS. 9D and 11D.

Figure 9E:
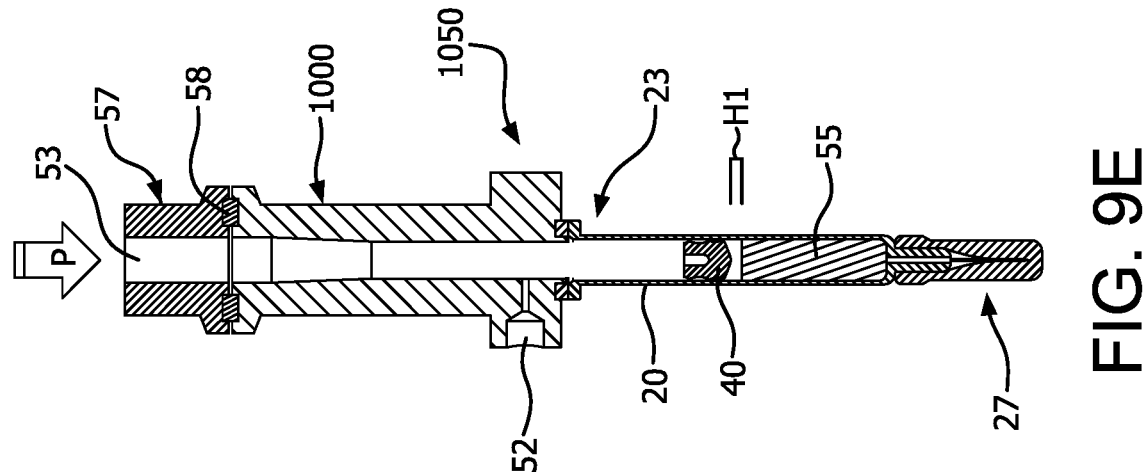
Figure 9D:
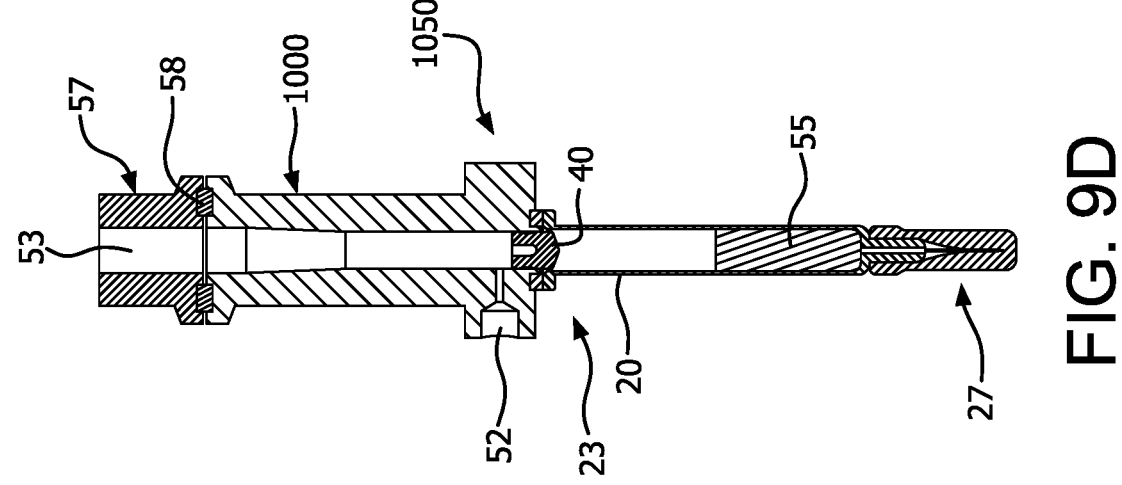
Figure 11E:
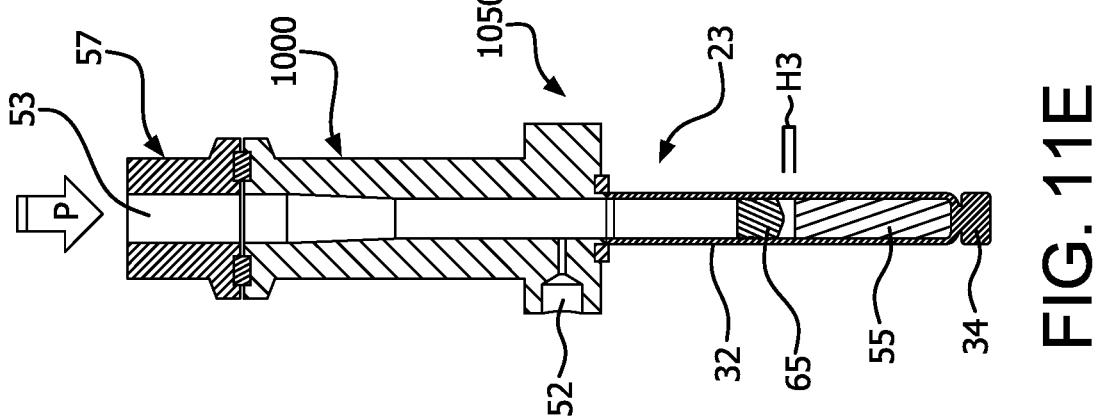
Figure 11D:
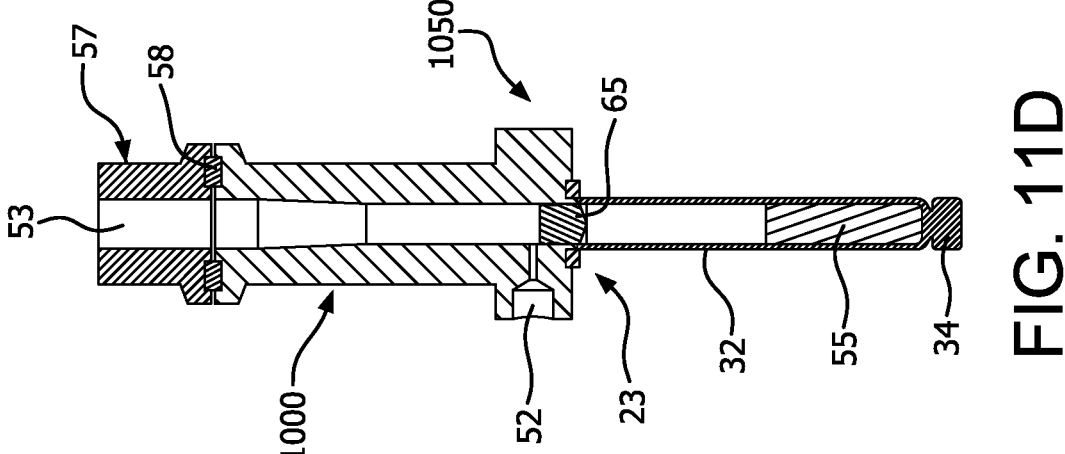

Looking next at FIGS. 9E and 11E, the stopper 40, 65 is translated through the barrel 20 or cartridge tube 32, decreasing the headspace H2 until the final desired headspace H1 is achieved. The stopper 40, 65 is translated by differential pressure created by the vacuum in the headspace H2 (created in the step depicted in FIGS. 9B and 11B) and a pressure P applied to the stopper 40, 65 by the pressure sealing cap 57 via the pressure port 53. In some embodiments, the pressure P may be atmospheric pressure and, in such embodiments, the pressure sealing cap 57 is not required. In some embodiments, the stopper 40, 65 is translated by an insertion rod 650 such as is depicted in FIGS. 8D and 10D. In some embodiments, the sealing of the vacuum chamber 1000 (see FIG. 9B), the application of vacuum (see FIG. 9C), the sealing of the pressure sealing cap 57 (see FIG. 9D), and the application of pressure (see FIG. 9E) occur simultaneously rather than sequentially.

In some embodiments, after the stopper 40, 65 has been placed in its final position, the pressure sealing cap 57 is retracted from the vacuum chamber 1000. The vacuum chamber 1000 may, either sequentially or simultaneously, be retracted so that the sealing gasket 1100 is removed from barrel flange 70 or sealing end portion 36 of the cartridge tube 32 (FIG. 9F and FIG. 11F).

Figure 12:
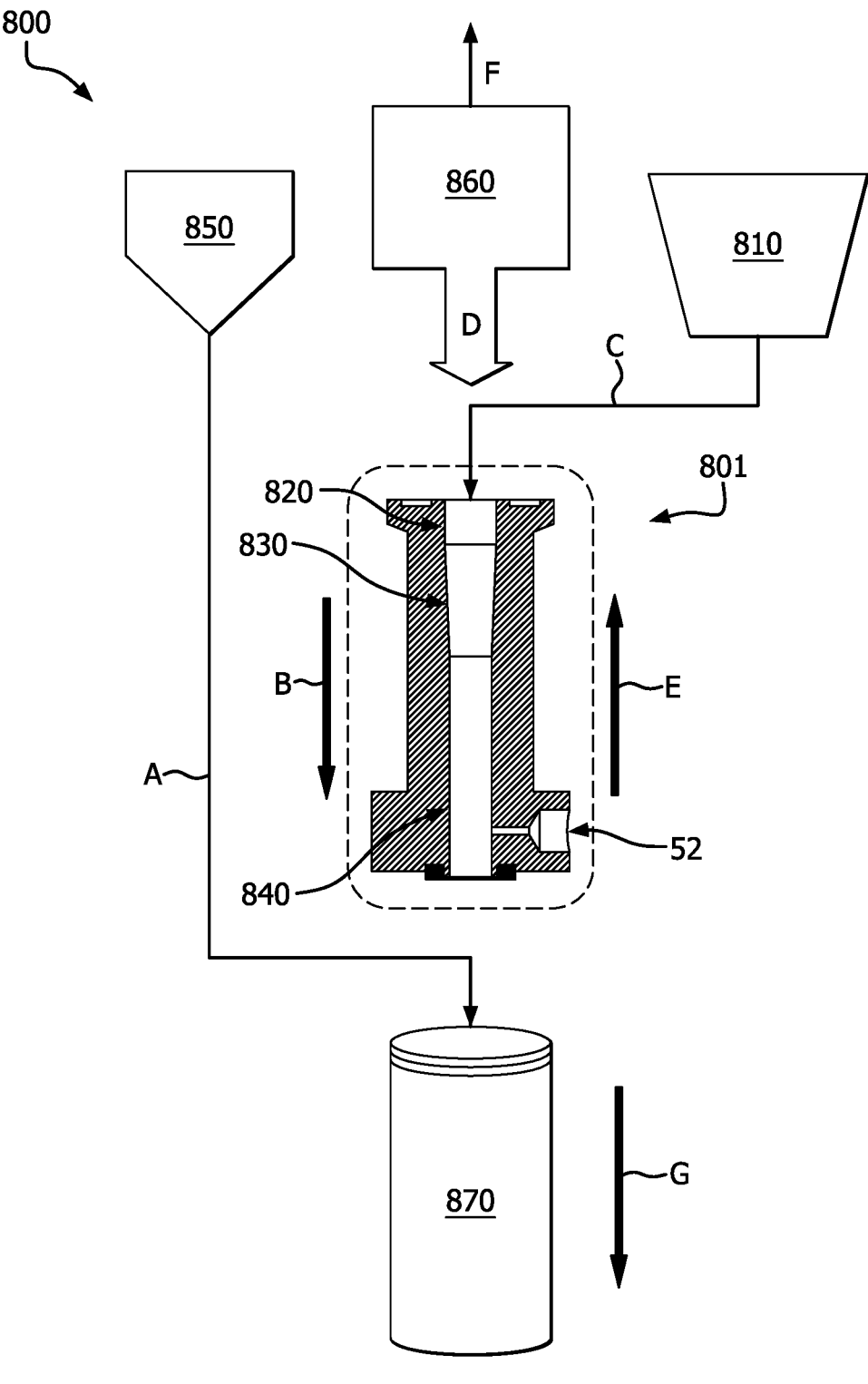
FIG. 12 depicts a system for assembling a lubricant free pre-filled syringe or cartridge.

An example of system 800 for assembling a pre-filled syringe or cartridge is depicted in FIG. 12. The system includes a stopper feeder 810 for providing non-lubricated free stoppers and a therapeutic compound feeder 850 for providing the therapeutic compound of interest to a syringe or cartridge. The system also includes a vacuum chamber 801 that has a placement region 820, a body 840, and a transition zone 830 having an angle that reduces the insertion diameter of the non-lubricated stoppers from the placement region 820 to the distal end of the body 840. The angle may range from about 0.1 degree to about 20 degrees, from about 0.05 degree to about 20 degrees, from about 1 degree to about 20 degrees, from about 3 degrees to about 20 degrees, from about 5 degrees to about 20 degrees, or from about 0.01 degree to about 15 degrees, from about 0.05 degree to about 15 degrees, from about 1 degree to about 15 degrees, from about 2 degrees to about 15 degrees, from about 3 degrees to about 15 degrees, from about 4 degrees to about 15 degrees, from about 5 degrees to about 15 degrees, from about 1 degree to 10 degrees, or from about 5 degrees to about 10 degrees.

The vacuum chamber also includes a vacuum port 52 for drawing a vacuum. The system 800 also includes at least one non-lubricated syringe barrel or non-lubricated cartridge tube 870 (or alternatively an array of syringe barrels or cartridge tubes) positioned to receive the vacuum chamber 801. In some embodiments, the system also includes a pressure member 860 that may be an insertion rod or a pneumatic force that provides for maneuvering the stopper in the vacuum chamber 801, where the maneuvering step is step D. In embodiments where a pressure differential created between a vacuum and atmospheric or higher than atmospheric pressure is utilized to translate the non-lubricated stopper or non-lubricated cartridge tube, the pressure member 860 would not be necessary, and may be removed from the system 800. The system 800 further includes mechanisms to lower the vacuum chamber 801 to sealably attach the non-lubricated syringe barrel or non-lubricated cartridge tube 870 to the vacuum chamber 801, in a process step B. In Step C, the lubricant free stopper is placed in the placement region 820. The system 800 includes a mechanism to remove the vacuum chamber 801 from the non-lubricated syringe barrel or non-lubricated cartridge tube 870 in a process step E and where an insertion rod is utilized, mechanisms to remove the pressure member 860 from the vacuum chamber 801 are also present in a process step F. In step G, the lubricant free stopper is translated down the non-lubricated syringe barrel or non-lubricated cartridge tube 870 with the pressure member 860 or by differential pressure.

In one embodiment, an active therapeutic is fed to the silicone free syringe barrel or cartridge tube in step A. Sequentially, or at the same time, the stopper (not shown) is removed from the stopper feeder 810 and is positioned in the placement region 820 in step C. The vacuum chamber 801 is lowered to sealably connect the non-lubricated syringe barrel or non-lubricated cartridge tube 870 in step B. The stopper is then maneuvered down to the distal end of body 840 in step D (either by differential pressure or by insertion pin or a combination thereof) and into the distal end of the syringe barrel or end portion of the cartridge tube, which is represented generally be reference numeral 870. In step G, the stopper is then maneuvered down to the desired position in the non-lubricated syringe barrel or non-lubricated cartridge tube 870 (either by differential pressure or by insertion pin or a combination thereof). In the next step, step E, the vacuum chamber 801 is backed away from the non-lubricated syringe barrel or non-lubricated cartridge tube 870. Finally in step F, the insertion rod or pressure sealing cap, if utilized, is backed away from the stopper and syringe barrel or cartridge tube 870. It is to be noted that the pressure member 860 and vacuum chamber 801 can be removed from the non-lubricated syringe barrel or non-lubricated cartridge tube 870 either sequentially or simultaneously.

In some embodiments, the insertion of the stopper into the syringe barrel or cartridge tube is considered to be successful if there are less than 10 lines formed (e.g., grooved or etched) on the front sealing rib of the stopper after insertion of the stopper 40 into one or more of the syringe barrel, the cartridge tube, or vacuum chamber. The lines are visible with the use of 100× magnification on an optical microscope (e.g., Keyence VHX-5000). In some embodiments, the front sealing rib of the stopper may have from 1 line to 20 lines, from 1 line to 15 lines, from 5 lines to 10 lines, from 1 line to 5 lines, or from 1 line to 3 lines. In some embodiments, the stopper does not have greater than 30 lines, as this is associated with a high probability of syringe or cartridge failure. In other embodiments, there may be no lines present on the front sealing rib of the stopper. Although not depicted pictorially, this "line count" method equally applies to determining the quality of a vacuum chamber, syringe barrel, or other component through which the stopper is moved to its final placement. In some embodiments, the internal surface of the body of the vacuum chamber creates less than 30 lines (e.g., from 1 to 30 lines) as measured on any rib in contact with the barrel or cartridge tube, such as, for example, the front sealing rib of the stopper. When there are less than 30 lines, there is less potential for the stopper seal to fail. In some aspects, there is less than or equal to 25 lines (e.g., 1 to 25 lines), less than or equal to 20 lines (e.g., 1 to 20 lines), less than or equal to 15 lines (e.g., 1 to 15 lines), less than or equal to 10 lines (e.g., 1 to 10 lines), less than or equal to 5 lines (e.g., 1 to 5 lines), or less than or equal to 3 lines (e.g., 1 to 3 lines).

In addition, the insertion of the stopper into the barrel or cartridge tube is considered to be successful if the helium leak rate of the stoppered syringe or cartridge is less than $1 \times 10^{-8}$ sccs or less than $1 \times 10^{-7}$ sccs. In some embodiments, the helium leak rate is not greater than $6 \times 10^{-6}$ sccs. The helium leak rate may be determined according to the method set forth in U.S. Pat. No. 10,471,211 to Rusch, et al. A description of the helium leak rate and results of the same are described in Example 1 below. It is to be appreciated that the helium leak rate may be used in the same manner as the "line count" method (described above) to determine the quality of a vacuum chamber, syringe barrel, cartridge tube, or other component through which the stopper is moved to its final placement.

In some embodiments, successful insertion (as defined by helium leak rate and/or line counts) of the lubricant free stopper in a lubricant free syringe barrel or lubricant free cartridge tube can be achieved by modifying the average surface roughness ($S_a$) of the inside surface of the vacuum chamber, barrel, or cartridge tube and/or the average kurtosis ($S_{ku}$) of the inside surface of the vacuum chamber, barrel, or cartridge tube. The target average surface roughness ($S_a$) and/or average kurtosis ($S_{ku}$) of the inside surface of the vacuum chamber, barrel, or cartridge tube can be achieved by a variety of methods known to one of ordinary skill in the art including, but not limited to, electropolishing, extrude honing, or a combination thereof. The test method for the average surface roughness ($S_a$) and average kurtosis ($S_{ku}$) and the results of the same are described in Example 1.

In some embodiments, the inside surface of the vacuum chamber, barrel, or cartridge tube may have an average surface roughness ($S_a$) from about 20 nm to about 400 nm, from about 20 nm to about 120 nm, from about 30 nm to about 80 nm, from about 30 nm to about 50 nm, from about 100 nm to about 300 nm, or from about 150 nm to about 250 nm. In some embodiments, the average surface roughness ($S_a$) is 25 nm or less. In addition, the inside surface of the vacuum chamber, barrel, or cartridge tube may have an average kurtosis ($S_{ku}$) from zero to less than about 3, from zero to less than about 4, from zero to less than about 5, from zero to less than about 6, from zero to less than about 7, or from zero to less than about 8. The insertion force combined with the average surface roughness ($S_a$) and/or average kurtosis ($S_{ku}$) define a space for the successful insertion of a stopper for each geometry of vacuum chamber, barrel, or cartridge tube.

At least the syringe barrel and stopper (e.g., syringe components) or the cartridge tube and stopper (e.g. cartridge components), vacuum chamber, and insertion pin (e.g., insertion components) are "lubricant free" or "substantially lubricant free." The term "lubricant free" as used herein is meant to denote that there are no lubricants of any kind, either intentionally or accidentally, added to the syringe barrel, cartridge tube, stopper, and/or to any equipment for manufacturing the same. Any amount of lubricant that may be present is only present in a trace amount (i.e., undetectable by any known measuring equipment or method). In some embodiments, however, lubricants may be inadvertently added through improper handling or residual lubricant on the manufacturing equipment; however, such lubricants may be present, so long as they are not intentionally added and are present in only a trace amount. It is to be appreciated that the needle of a syringe barrel purposefully has a lubricant thereon for ease of insertion into a patient. However, the needle is not considered to be within the purview of the present disclosure.

The term "substantially lubricant free" is meant to denote that there may be an amount of lubricant (e.g., silicone) present that is detectable by any known measuring equipment or method. In some embodiments, this means that there may be from about 0 µg to about 5 µg, from about 1 µg to about 5 µg, or from about 2 µg to about 5 µg of lubricant present on the inner surface of the syringe. The absence or substantial absence of lubricants (e.g., silica) can be measured using gas chromatography (GC) mass spectrometry or inductively coupled plasma (ICP) mass spectrometry. Substantially lubricant free may also or alternatively be measured by the amount of particles in the syringe barrel that are measured in water for injection (WFI) after the WFI has been exposed to a fully assembled syringe (e.g., a glass barrel and stopper and alternatively at least one therapeutic compound). In some embodiments, the amount of particles in the barrel may be less than about 600 particles/mL for particles greater than 10 µm in size or less than 60 particles/mL for particles greater than 25 µm in size when measured in WFI.

In some embodiments, lubricants other than silicone-based lubricants may be permitted. Common silicone-based lubricants include silicone oil or silicone grease, siloxanes, polysiloxane, organosiloxane, polyorganosiloxane, silicate esters, and similar compounds and combination thereof. In other embodiments, water based lubricants (e.g., polyethylene glycol, glycerin, cellulose ether), oil based lubricants (e.g., as petroleum jelly, paraffins, and olefins), and combinations thereof may be present on the inner surface of the syringe barrel or cartridge tube. In further embodiments, there may be no lubricant of any kind present on the inner surface of the syringe barrel or cartridge tube, but there may be a finish or a polish on the syringe barrel or cartridge tube.

It is to be appreciated that the ranges described herein may be utilized in conjunction with a 0.5 mL up to and including a 20 mL syringe or cartridge, but may be appropriately scaled to smaller or larger syringes or cartridges. It should also be understood that one or more design features of the syringes and cartridges described herein can be combined with other features of other syringes and cartridges described herein.

In another aspect, the syringe barrel, the cartridge tube, the plunger rod, and the stopper described herein may be used in combination with different therapeutic compounds such as, for example, drugs and biologics, including but not limited to, antibodies, antisense, RNA interference, gene therapy, primary and embryonic stem cells, vaccines, and combinations thereof. For instance, the embodiments described herein may be utilized in combination with any or all of the following biologics and/or therapeutic compounds.

Cell therapy using cells that are derived primarily from endoderm such as Exocrine secretory epithelial cells and Hormone-secreting cells; ectoderm such as Keratinizing epithelial cells, Wet stratified barrier epithelial cells, Sensory transducer cells, Autonomic neuron cells, Sense organ and peripheral neuron supporting cells, Central nervous system neurons and glial cells, Lens cells; mesoderm such as Metabolism and storage cells, Barrier function cells (lung, gut, exocrine glands, and urogenital tract), Extracellular matrix cells, Contractile cells, Blood and immune system cells, Germ cells, Nurse cell, Interstitial cells or a combination thereof. Additionally cells that are genetically, chemically or physically altered or modified are considered to be in the scope of the disclosure.

Examples of Exocrine secretory epithelial cells include, but are not limited to, Salivary gland mucous cell, Salivary gland number 1, Von Ebner's gland cell in tongue, Mammary gland cell, Lacrimal gland cell, Ceruminous gland cell in ear, Eccrine sweat gland dark cell, Eccrine sweat gland clear cell, Apocrine sweat gland cell, Gland of Moll cell in eyelid, Sebaceous gland cell, Bowman's gland cell in nose, Brunner's gland cell in duodenum, Seminal vesicle cell, Prostate gland cell, Bulbourethral gland cell, Bartholin's gland cell, Gland of Littre cell, Uterus endometrium cell, Isolated goblet cell of respiratory and digestive tracts, Stomach lining mucous cell, Gastric gland zymogenic cell, Gastric gland oxyntic cell, Pancreatic acinar cell, Paneth cell of small intestine, Type II pneumocyte of lung, Clara cell of lung; Hormone-secreting cells including but not limited to: Anterior pituitary cells, Intermediate pituitary cell, Magnocellular neurosecretory cells, Gut and respiratory tract cells, Thyroid gland cells, Parathyroid gland cells, Adrenal gland cells, Leydig cell of testes secreting testosterone, Theca internal cell of ovarian follicle secreting estrogen, Corpus *luteum* cell of ruptured ovarian follicle secreting progesterone, Juxtaglomerular cell, Macula *densa* cell of kidney, Peripolar cell of kidney, Mesangial cell of kidney, Pancreatic islets; Keratinizing epithelial cells including but not limited to: Epidermal keratinocyte, Epidermal basal cell, Keratinocyte of fingernails and toenails, Nail bed basal cell, Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell; Wet stratified barrier epithelial cells including but not limited to: Surface epithelial cell of stratified squamous epithelium and basal cell of epithelia of cornea, tongue, oral cavity, esophagus, anal canal, distal urethra and vagina, Urinary epithelium cell; Sensory transducer cells including but not limited to: Auditory inner hair cell of organ of *Corti*, Auditory outer hair cell of organ of *Corti*, Basal cell of olfactory epithelium, Cold-sensitive primary sensory neurons, Heat-sensitive primary sensory neurons, Merkel cell of epidermis, Olfactory receptor neuron, Pain-sensitive primary sensory neurons, Photoreceptor cells of retina in eye: Proprioceptive primary sensory neurons, Touch-sensitive primary sensory neurons, Type I carotid body cell, Type II carotid body cell, Type I hair cell of vestibular system of ear, Type II hair cell of vestibular system of ear, Type I taste bud cell; Autonomic neuron cells including but not limited to: Cholinergic neural cell, Adrenergic neural cell, Peptidergic neural cell; Sense organ and peripheral neuron supporting cells including but not limited to: Inner pillar cell of organ of *Corti*, Outer pillar cell of organ of *Corti*, Inner phalangeal cell of organ of *Corti*, Outer phalangeal cell of organ of *Corti*, Border cell of organ of *Corti*, Hensen cell of organ of *Corti*, Vestibular apparatus supporting cell, Taste bud supporting cell, Olfactory epithelium supporting cell, Schwann cell, Satellite glial cell, Enteric glial cell; Central nervous system neurons and glial cells including but not limited to: Astrocyte, Neuron cells, Oligodendrocyte, Spindle neuron; Lens cells including but not limited to: Anterior lens epithelial cell, Crystallin-containing lens fiber cell; Metabolism and storage cells including but not limited to: Adipocytes: Liver lipocyte; Barrier function cells including but not limited to: Kidney parietal cell, Kidney glomerulus podocyte, Kidney proximal tubule brush border cell, Loop of Henle thin segment cell, Kidney distal tubule cell, Kidney collecting duct cell, Principal cells, Intercalated cells, Type I pneumocyte, Pancreatic duct cell, Nonstriated duct cell, Principal cell, Intercalated cell, Duct cell, Intestinal brush border cell, Exocrine gland striated duct cell, Gall bladder epithelial cell, Ductulus efferens nonciliated cell, Epididymal principal cell, Epididymal basal cell; Extracellular matrix cells including but not limited to: Ameloblast epithelial cell, Planum semilunatum epithelial cell of vestibular system of ear, Organ of *Corti* interdental epithelial cell, Loose connective tissue fibroblasts, Corneal fibroblasts, Tendon fibroblasts, Bone marrow reticular tissue fibroblasts, Other nonepithelial fibroblasts, Pericyte, Nucleus pulposus cell of intervertebral disc, Cementoblast/cementocyte, Odontoblast/odontocyte, Hyaline cartilage chondrocyte, Fibrocartilage chondrocyte, Elastic cartilage chondrocyte, Osteoblast/osteocyte, Osteoprogenitor cell, Hyalocyte of vitreous body of eye, Stellate cell of perilymphatic space of ear, Hepatic stellate cell, Pancreatic stelle cell; Contractile cells including but not limited to: Skeletal muscle cell, Satellite cell, Heart muscle cells, Smooth muscle cell, Myoepithelial cell of iris, Myoepithelial cell of exocrine glands; Blood and immune system cells including but not limited to: Erythrocyte, Megakaryocyte, Monocyte, Connective tissue macrophage, Epidermal Langerhans cell, Osteoclast, Dendritic cell, Microglial cell, Neutrophil granulocyte, Eosinophil granulocyte, Basophil granulocyte, Hybridoma cell, Mast cell, Helper T cell, Suppressor T cell, Cytotoxic T cell, Natural Killer T cell, B cell, Natural killer cell, Reticulocyte, Stem cells and committed progenitors for the blood and immune system; Germ cells including but not limited to: Oogonium/Oocyte, Spermatid, Spermatocyte, Spermatogonium cell, Spermatozoon; Nurse cell including but not limited to: Ovarian follicle cell, Sertoli cell, Thymus epithelial cell; Interstitial cells including but not limited to: Interstitial kidney cells and a combination thereof.

Examples of antibodies, antisense, RNA interference, or gene therapy made to protein targets or gene(s) of: Ataxia Telangiectasia Mutated, Tumor Protein p53, Checkpoint kinase 2, breast cancer susceptibility protein, Double-strand break repair protein, DNA repair protein RAD50, Nibrin, p53-binding protein, Mediator of DNA damage checkpoint protein, H2A histone family member X, Microcephalin, C-terminal-binding protein 1, Structural maintenance of chromosomes protein 1A; Esterases; Phosphatases; Examples of Ion channels include but are not limited to: ligand-gated ion channels, voltage-gated ion channels; Examples of growth factors include but are not limited to: nerve growth factor (NGF), vascular endothelial growth factor (VEGF), platelet-derived growth factor (PDGF), C-fos-induced growth factor (FIGF), platelet-activating factor (PAF), transforming growth factor beta (TGF-8), b, one morphogenetic proteins (BMPs), Activin, inhibin, fibroblast growth factors (FGFs), granulocyte-colony stimulating factor (G-CSF), granulocyte-macrophage colony stimulating factor (GM-CSF), glial cell line-derived neurotrophic factor (GDNF), growth differentiation factor-9 (GDF9), epidermal growth factor (EGF), transforming growth factor-α (TGF-α), growth factor (KGF), migration-stimulating factor (MSF), hepatocyte growth factor-like protein (HGFLP), hepatocyte growth factor (HGF), hepatoma-derived growth factor (HDGF), Insulin-like growth factors; Examples of G Protein-Coupled Receptors (GPCR) include but are not limited to: Adenosine receptor family, Adrenergic receptor family, Angiotensin II receptor, Apelin receptor, Vasopressin receptor family, Brain-specific angiogenesis inhibitor family, Bradykinin receptor family, Bombesin receptor family, Complement component 3a receptor 1, Complement component 5a receptor 1, Calcitonin receptor family, Calcitonin receptor-like family, Calcium-sensing receptor, Cholecystokinin A receptor (CCK1), Cholecystokinin B receptor (CCK2), Chemokine (C-C motif) receptor family, Sphingosine 1-phosphate receptor family, Succinic receptor, Cholinergic receptor family, Chemokine-like receptor family, Cannabinoid receptor family, Corticotropin releasing hormone receptor family, prostaglandin D2 receptor, Chemokine C-X3-C receptor family, Chemokine (C-X-C motif) receptor family, Burkitt lymphoma receptor, Chemokine (C-X-C motif) receptor family, Cysteinyl leukotriene receptor 2 (CYSLT2), chemokine receptor (FY), Dopamine receptor family, G protein-coupled receptor 183 (GPR183), Lysophosphatidic acid receptor family, Endothelin receptor family, Coagulation factor II (thrombin) receptor family, Free fatty acid receptor family, Formylpeptide receptor family, Follicle stimulating hormone receptor (FSHR), gamma-aminobutyric acid (GABA) B receptor, Galanin receptor family, Glucagon receptor, Growth hormone releasing hormone receptor (GHRH), Ghrelin receptor (ghrelin), Growth hormone secretagogue receptor 1b (GHSR1b), Gastric inhibitory polypeptide receptor (GIP), Glucagon-like peptide receptor family, Gonadotropin-releasing hormone receptor (GnRH), pyroglutamylated RFamide peptide receptor (QRFPR), G protein-coupled bile acid receptor 1 (GPBA), Hydroxycarboxylic acid receptor family, Lysophosphatidic acid receptor 4 (LPA4) Lysophosphatidic acid receptor 5 (GPR92), G protein-coupled receptor 79 pseudogene (GPR79), Hydroxycarboxylic acid receptor 1 (HCA1), G-protein coupled receptor (C5L2, FFA4, FFA4, FFA4, GPER, GPR1, GPR101, GPR107, GPR119, GPR12, GPR123, GPR132, GPR135, GPR139, GPR141, GPR142, GPR143, GPR146, GPR148, GPR149, GPR15, GPR150, GPR151, GPR152, GPR157, GPR161, GPR162, GPR17, GPR171, GPR173, GPR176, GPR18, GPR182, GPR20, GPR22, GPR25, GPR26, GPR27, GPR3, GPR31, GPR32, GPR35, GPR37L1, GPR39, GPR4, GPR45, GPR50, GPR52, GPR55, GPR6, GPR61, GPR65, GPR75, GPR78, GPR83, GPR84, GPR85, GPR88, GPR97, TM7SF1), Metabotropic glutamate receptor family, Gastrin releasing peptide receptor (BB2), Orexin receptor family, Histamine receptor family, 5-hydroxytryptamine receptor family, KISS1-derived peptide receptor (kisspeptin), Leucine-rich repeat-containing G protein-coupled receptor family, horiogonadotropin receptor (LH), Leukotriene B4 receptor (BLT1), Adenylate Cyclase Activating Polypeptide 1 Receptor 1 (mPAC1), Motilin receptor, Melanocortin receptor family, Melanin concentrating hormone receptor 1 (MCH1), Neuropeptide Y1 receptor (Y1), Neuropeptide Y2 receptor (NPY2R), Opioid receptor family, Oxytocin recepter (OT), P2Y Purinoceptor 12 (mP2Y12), P2Y Purinoceptor 6 (P2Y6), Pancreatic polypeptide receptor family, Platelet-activating factor receptor family, Prostaglandin E receptor family, Prostanoid IP1 receptor (IP1), MAS-related GPR, member family, Rhodopsin (Rhodopsin), Relaxin family peptide receptor family, Somatostatin receptor family, Tachykinin receptor family, Melatonin receptor family, Urotensin receptor family, Vasoactive intestinal peptide receptor 1 (mVPAC1), Neuromedin B Receptor (BB1), Neuromedin U receptor 1 (NMU1), Neuropeptides B/W receptor family, Neuropeptide FF receptor 1 (NPFF1), neuropeptide S receptor 1 (NPS receptor), Neuropeptide Y receptor family, Neurotensin receptor 1 (NTS1), Opsin 5 (OPN5), Opioid receptor-like receptor (NOP), Oxoeicosanoid (OXE) receptor 1 (OXE), Oxoglutarate (alpha-ketoglutarate) receptor 1 (OXGR1), Purinergic receptor family, Pyrimidinergic receptor family, Prolactin releasing hormone receptor (PRRP), Prokineticin receptor family, Platelet activating receptor (PAF), Prostaglandin F receptor family, Prostaglandin 12 (prostacyclin) receptor family, Parathyroid hormone receptor family, muscarinic 4 (rM4), Prostanoid DP2 receptor (rGPR44), Prokineticin receptor family, Relaxin family peptide receptor family, Secretin receptor (secretin), Smoothened, Frizzled class receptor (Smoothened), trace amine associated receptor family, Tachykinin family, Thromboxane A2 receptor (TP), Thyrotropin-releasing hormone receptor (TRH1), Thyroid Stimulating Hormone Receptor (TSH); Examples of Protein kinases include but are not limited to: AP2 associated kinase, *Homo sapiens* ABL proto-oncogene 1-non-receptor tyrosine-protein kinase family, c-abl oncogene 1 receptor tyrosine kinase family, v-abl Abelson murine leukemia viral oncogene homolog 2, activin A receptor family, chaperone—ABC1 activity of bc1 complex homolog (*S. pombe*) (ADCK3), aarF domain containing kinase 4 (ADCK4), v-akt murine thymoma viral oncogene homolog family, anaplastic lymphoma receptor tyrosine kinase family, protein kinase A family, protein kinase B family, ankyrin repeat and kinase domain containing 1 (ANKK1), NUAK family—SNF1-like kinase, mitogen-activated protein kinase family aurora kinase A (AURKA), aurora kinase B (AURKB), aurora kinase C (AURKC), AXL receptor tyrosine kinase (AXL), BMP2 inducible kinase (BIKE), B lymphoid tyrosine kinase (BLK), bone morphogenetic protein receptor family, BMX non-receptor tyrosine kinase (BMX), v-raf murine sarcoma viral oncogene homolog B1 (BRAF), protein tyrosine kinase 6 (BRK), BR serine/threonine kinase family, Bruton agammaglobulinemia tyrosine kinase (BTK), calcium/calmodulin-dependent protein kinase family, cyclin-dependent kinase family, cyclin-dependent kinase-like family, CHK1 checkpoint homolog (*S. pombe*) (CHEK1), CHK2 checkpoint homolog (*S. pombe*) (CHEK2), Insulin receptor, isoform A (INSR), Insulin receptor, isoform B (INSR), rho-interacting serine/threonine kinase (CIT), v-kit Hardy-Zuckerman 4 feline sarcoma viral oncogene homolog (KIT), CDC-Like Kinase family—Hepatocyte growth factor receptor (MET), Proto-oncogene tyrosine-protein kinase receptor, colony-stimulating factor family receptor, c-src tyrosine kinase (CSK), casein kinase family, megakaryocyte-associated tyrosine kinase (CTK), death-associated protein kinase family, doublecortin-like kinase family, discoidin domain receptor tyrosine kinase, dystrophia myotonica-protein kinase (DMPK), dual-specificity tyrosine-(Y)-phosphorylation regulated kinase family, epidermal growth factor receptor family, eukaryotic translation initiation factor 2-alpha kinase 1 (EIF2AK1), EPH receptor family, Ephrin type-A receptor family, Ephrin type-B receptor family, v-erb-b2 erythroblastic leukemia viral oncogene homolog family, mitogen-activated protein kinase family, endoplasmic reticulum to nucleus signaling 1 (ERN1), PTK2 protein tyrosine kinase 2 (FAK), fer (fps/fes related) tyrosine kinase (FER). feline sarcoma oncogene (FES), Fibroblast growth factor receptor family, Gardner-Rasheed feline sarcoma viral (v-fgr) oncogene homolog (FGR), fms-related tyrosine kinase family, Fms-related tyrosine kinase family, fyn-related kinase (FRK), FYN oncogene related to SRC, cyclin G associated kinase (GAK), eukaryotic translation initiation factor 2 alpha kinase, Growth hormone receptor. G protein-coupled receptor kinase 1 (GRK1), G protein-coupled receptor kinase family, glycogen synthase kinase family, germ cell associated 2 (haspin) (HASPIN), Hemopoietic cell kinase (HCK), homeodomain interacting protein kinase family, mitogen-activated protein kinase family, hormonally up-regulated Neu-associated kinase (HUNK), intestinal cell (MAK-like) kinase (ICK), Insulin-like growth factor 1 receptor (IGF1R), conserved helix-loop-helix ubiquitous kinase (IKK-alpha), inhibitor of kappa light polypeptide gene enhancer in B-cells—kinase beta family, insulin receptor (INSR), insulin receptor-related receptor (INSRR), interleukin-1 receptor-associated kinase family, IL2-inducible T-cell kinase (ITK), Janus kinase family, Kinase Insert Domain Receptor, v-kit Hardy-Zuckerman 4 feline sarcoma viral oncogene homolog, lymphocyte-specific protein tyrosine kinase (LCK), LIM domain kinase family, serine/ threonine kinase family leucine-rich repeat kinase family, v-yes-1 Yamaguchi sarcoma viral related oncogene homolog (LYN), male germ cell-associated kinase (MAK), MAP/microtubule affinity-regulating kinase family, microtubule associated serine/threonine kinase family, maternal embryonic leucine zipper kinase, c-mer proto-oncogene tyrosine kinase (MERTK), met proto-oncogene (hepatocyte growth factor receptor), MAP kinase interacting serine/threonine kinase family, myosin light chain kinase family, mixed lineage kinase domain-like protein isoform, CDC42 binding protein kinase family, serine/threonine kinase family, macrophage stimulating 1 receptor (c-met-related tyrosine kinase) (MST1R), mechanistic target of rapamycin (serine/threonine kinase) (MTOR), muscle-skeletal-receptor tyrosine kinase (MUSK), myosin light chain kinase family, NIMA (never in mitosis gene a)-related kinase family, serine/threonine-protein kinase NIM1 (NIM1), nemo-like kinase (NLK), oxidative-stress responsive 1 (OSR1), p21 protein (Cdc42/Rac)-activated kinase family, PAS domain containing serine/threonine kinase, Platelet-derived growth factor receptor family, 3-phosphoinositide dependent protein kinase-1 (PDPK1), Calcium-dependent protein kinase 1, phosphorylase kinase gamma family, Phosphatidylinositol 4,5-bisphosphate 3-kinase, phosphoinositide-3-kinase family, phosphatidylinositol 4-kinase family. phosphoinositide kinase, FYVE finger containing, Pim-1 oncogene (PIM1), pim-2 oncogene (PIM2), pim-3 oncogene (PIM3), phosphatidylinositol-4-phosphate 5-kinase family, phosphatidylinositol-5-phosphate 4-kinase family protein kinase, membrane associated tyrosine/threonine 1 (PKMYT1), protein kinase N family, polo-like kinase family, protein kinase C family, protein kinase D family, cGMP-dependent protein kinase family, eukaryotic translation initiation factor 2-alpha kinase 2 (PRKR), X-linked protein kinase (PRKX), Prolactin receptor (PRLR), PRP4 pre-mRNA processing factor 4 homolog B (yeast) (PRP4), PTK2B protein tyrosine kinase 2 beta (PTK2B), SIK family kinase 3 (QSK), v-raf-1 murine leukemia viral oncogene homolog 1 (RAF1), Neurotrophic tyrosine kinase receptor type family, receptor (TNFRSF)-interacting serine-threonine kinase family, dual serine/threonine and tyrosine protein kinase (RIPK5), Rho-associated, coiled-coil containing protein kinase family, c-ros oncogene 1, receptor tyrosine kinase (ROS1), ribosomal protein S6 kinase family, SH3-binding domain kinase 1 (SBK1), serum/glucocorticoid regulated kinase family, Putative uncharacterized serine/threonine-protein kinase (Sugen kinase 110) (SgK110), salt-inducible kinase family, SNF related kinase (SNRK), src-related kinase, SFRS protein kinase family, Spleen tyrosine kinase (SYK), TAO kinase family, TANK-binding kinase 1 (TBK1), tec protein tyrosine kinase (TEC), testis-specific kinase 1 (TESK1), transforming growth factor, beta receptor family, tyrosine kinase with immunoglobulin-like and EGF-like domains 1 (TIE1), TEK tyrosine kinase, endothelial (TIE2), Angiopoietin-1 receptor (Tie2), tousled-like kinase family, TRAF2 and NCK interacting kinase (TNIK), non-receptor tyrosine kinase family, TNNI3 interacting kinase (TNNI3K), transient receptor potential cation channel, testis-specific serine kinase family, TTK protein kinase (TTK), TXK tyrosine kinase (TXK), Tyrosine kinase 2 (TYK2), TYRO3 protein tyrosine kinase (TYRO3), unc-51-like kinase family, phosphatidylinositol 3-kinase, vaccinia related kinase 2 (VRK2), WEE1 homolog family, WNK lysine deficient protein kinase family, v-yes-1 Yamaguchi sarcoma viral oncogene homolog 1 (YES), sterile alpha motif and leucine zipper containing kinase AZK (ZAK), zeta-chain (TCR) associated protein kinase 70 kDa (ZAP70); Examples of nuclear hormone receptors include but are not limited to: Androgen receptor (AR), Estrogen related receptor alpha (ESRRA), Estrogen receptor 1 (ESR1), Nuclear receptor subfamily 1-group H-member 4 (NR1H4), Nuclear receptor subfamily 3-group C-member 1 (glucocorticoid receptor) (NR3C1), Nuclear receptor subfamily 1-group H-member 3 (Liver X receptor a) (NR1H3), Nuclear receptor subfamily 1-group H-member 2 (Liver X receptor 13) (NR1H2), Nuclear receptor subfamily 1-group H-member 2 (Liver X receptor 13) (NR1H2), Nuclear receptor subfamily 3-group C-member 2 (Mineralcorticoid receptor) (NR3C2), Peroxisome Proliferator Activated Receptor alpha (PPARA), Peroxisome Proliferator Activated Receptor gamma (PPARG), Peroxisome Proliferator Activated Receptor delta (PPARD), Progesterone receptor a (PGR), Progesterone receptor 13 (PGR), Retinoic acid receptor-alpha (RARA), Retinoic acid receptor-beta (RARB), Retinoid X receptor-alpha (RXRA), Retinoid X receptor-gamma (RXRG), Thyroid hormone receptor-alpha (THRA), Thyroid hormone receptor-beta (THRB), Retinoic acid-related orphan receptor, Liver X receptor, Farnesoid X receptor, Vitamin D receptor, Pregnane X receptor, Constitutive androstane receptor, Hepatocyte nuclear factor 4, Oestrogen receptor, Oestrogen-related receptor, Glucocortioic receptor, Nerve growth factor-induced-B, Germ cell nuclear factor; Examples of Epigenetic targets include but are not limited to: ATPase family AAA domain-containing protein 2 (ATAD2A), ATPase family-AAA domain containing 2B (ATAD2B), ATPase family AAA domain containing-2B (ATAD2B), bromodomain adjacent to zinc finger domain-1A (BAZ1A), bromodomain adjacent to zinc finger domain-1B (BAZ1B), bromodomain adjacent to zinc finger domain-2A (BAZ2A), bromodomain adjacent to zinc finger domain-2A (BAZ2A), bromodomain adjacent to zinc finger domain-2B (BAZ2B), bromodomain-containing protein 1 (BRD1), Bromodomain containing protein 2-1st bromodomain (BRD2), Bromodomain containing protein 2-1st & 2nd bromodomains (BRD2), bromodomain-containing protein 2 isoform 1-bromodomain 2 (BRD2(2)), bromodomain-containing protein 3-bromodomain 1 (BRD3(1)), Bromodomain-containing protein 3-1st bromodomain (BRD3), Bromodomain-containing protein 3-1st & 2nd bromodomains (BRD3), bromodomain-containing protein 3-bromodomain 2 (BRD3(2)), Bromodomain containing protein 4-1st bromodomain (BRD4), bromodomain-containing protein 4 isoform long-bromodomains 1 and 2 (BRD4(1-2)), bromodomain-containing protein 4 isoform long-bromodomain 2 (BRD4(2)), bromodomain-containing protein 4 isoform short (BRD4(full-length-short-iso.)), Bromodomain containing protein 7 (BRD7), bromodomain containing 8-bromodomain 1 (BRD8(1)), bromodomain containing 8-bromodomain 2 (BRD8(2)), bromodomain-containing protein 9 isoform 1 (BRD9), Bromodomain containing testis-specific-1st bromodomain (BRDT), Bromodomain containing testis-specific-1st & 2nd bromodomains (BRDT), bromodomain testis-specific protein isoform b-bromodomain 2 (BRDT (2)), bromodomain and PHD finger containing-1 (BRPF1), bromodomain and PHD finger containing-3 (BRPF3), bromodomain and PHD finger containing-3 (BRPF3), Bromodomain and WD repeat-containing 3-2nd bromodomain (BRWD3(2)), Cat eye syndrome critical region protein 2 (CECR2), CREB binding protein (CREBBP), E1A binding protein p300 (EP300), EP300 (EP300), nucleosome-remodeling factor subunit BPTF isoform 1 (FALZ), Nucleosome-remodeling factor subunit BPT (FALZ), Euchromatic histone-lysine N-methyltransferase 2 (EHMT2), Histone Acetyltransferase-KAT2A (GCN5L2), Euchromatic histone-lysine N-methyltransferase 1 (EHMT1), Histone-lysine N-methyltransferase MLL (MLL), Polybromo 1-1st bromodomain (PB1(1)), Polybromo 1-2nd bromodomain (PB1 (2)), polybromo 1-bromodomain 2 (PBRM1(2)), polybromo 1-bromodomain 5 (PBRM1(5)), Histone acetyltransferase KAT2B (PCAF), PH-interacting protein-1st bromodomain (PHIP(1)), PH-interacting protein-2nd bromodomain (PHIP (2)), Protein kinase C-binding protein 1 (PRKCBP1), Protein arginine N-methyltransferase 3 (PRMT3), SWI/SNF related-matrix associated-actin dependent regulator of chromatin-subfamily a-member 2 (SMARCA2), SWI/SNF related-matrix associated-actin dependent regulator of chromatin-subfamily a-member 4 (SMARCA4), Nuclear body protein-SP110 (SP110), Nuclear body protein-SP140 (SP140), Transcription initiation factor TFIID subunit 1 (TAF1(1-2)), TAF1 RNA polymerase II-TATA box binding protein (TBP)-associated factor-250 kDa-bromodomain 2 (TAF1(2)), Transcription initiation factor TFIID subunit 1-like-1st bromodomain (TAF1L(1)), Transcription initiation factor TFIID subunit 1-like-2nd bromodomain (TAF1L (2)), tripartite motif containing 24 (TRIM24(Bromo.)), tripartite motif containing 24 (TRIM24(PHD-Bromo.)), E3 ubiquitin-protein ligase TRIM33 (TRIM33), tripartite motif containing 33 (TRIM33(PHD-Bromo.)), WD repeat 9-1st bromodomain (WDR9(1)), WD repeat 9-2nd bromodomain (WDR9(2)); membrane transport proteins including but not limited to ATP-binding cassette (ABC) superfamily, solute carrier (SLC) superfamily, multidrug resistance protein 1 (P-glycoprotein), organic anion transporter 1, and protein such as EAAT3, EAAC1, EAAT1, GLUT1, GLUT2, GLUT9, GLUT10, rBAT, AE1, NBC1, KNBC, CHED2, BTR1, NABC1, CDPD, SGLT1, SGLT2, NIS, CHT1, NET, DAT, GLYT2, CRTR, BOAT1, SIT1, XT3, y+LAT1, BAT1, NHERF1, NHE6, ASBT, DMT1, DCT1, NRAMP2, NKCC2, NCC, KCC3, NACT, MCT1, MCT8, MCT12, SLD, VGLUT3, THTR1, THTR2, PIT2, GLVR2, OCTN2, URAT1, NCKX1, NCKX5, CIC, PiC, ANT1, ORNT1, AGC1, ARALAR, Citrin, STLN2, aralar2, TPC, MUP1, MCPHA, CACT, GC1, PHC, DTD, CLD, DRA, PDS, Prestin, TAT1, FATP4, ENT3, ZnT2, ZnT10, AT1, NPT2A, NPT2B, HHRH, CST, CDG2F, UGAT, UGTL, UGALT, UGT1, UGT2, FUCT1, CDG2C, NST, PAT2, G6PT1, SPX4, ZIP4, LIV4, ZIP13, LZT-Hs9, FPN1, MTP1, IREG1, RHAG, AIM1, PCFT, FLVCR1, FLVCR2, RFT1, RFT2, RFT3, OATP1B1, OATP1B3, OATP2A1; structural proteins including but not limited to tubulin, heat shock protein, Microtubule-stabilizing proteins, Oncoprotein 18, stathmin, kinesin-8 and kinesin-14 family, Kip3, Kif18A; proteases including but not limited ADAM (a disintegrin and metalloprotease) family; Other molecule targets in signal transductions include but are not limited to: Cell division cycle 25 homolog A (CDC25A), forkhead box 03 (forkhead box 03), nuclear factor of kappa light polypeptide gene enhancer in B-cells inhibitor, alpha (NFKBIA), nuclear factor (erythroid-derived 2)-like 2 (NFE2L2), Natriuretic peptide receptor A (NPR1), Tumor necrosis factor receptor superfamily, member 11a (TNFRSF11A), v-rel reticuloendotheliosis viral oncogene homolog A (avian) (RELA), Sterol regulatory element binding transcription factor 2 (SREBF2), CREB regulated transcription coactivator 1 (CRTC1), CREB regulated transcription coactivator 2 (CRTC2), X-box binding protein 1 (XBP1), Catenin (cadherin-associated protein), beta 1 (CTNNB1), and combinations thereof.

Examples of known biologics include, but are not limited to: Abbosynagis, Abegrin, Actemra, AFP-Cide, Antova, Arzerra, Aurexis, Avastin, Benlysta, Bexxar, Blontress, Bosatria, Campath, CEA-Cide, CEA-Scan, Cimzia, Cyramza, Ektomab, Erbitux, FibriScint, Gazyva, Herceptin, hPAM4-

Cide, HumaSPECT, HuMax-CD4, HuMax-EGFr, Humira, HuZAF, Hybri-ceaker, Ilaris, Indimacis-125, Kadcyla, Lemtrada, LeukArrest, LeukoScan, Lucentis, Lymphomun, LymphoScan, LymphoStat-B, MabThera, Mycograb, Mylotarg, Myoscint, NeutroSpec, Numax, Nuvion, Omnitarg, Opdivo, Orthoclone OKT3, OvaRex, Panorex, Prolia, Prostascint, Raptiva, Remicade, Removab, Rencarex, ReoPro, Rexomun, Rituxan, RoActemra, Scintimun, Simponi, Simulect, Soliris, Stelara, Synagis, Tactress, Theracim, Theragyn, Theraloc, Tysabri, Vectibix, Verluma, Xolair, Yervoy, Zenapax, and Zevalin or combinations thereof.

Examples of known monoclonal antibodies include but are not limited to: 3F8, 8H9, Abagovomab, Abciximab, Abituzumab, Abrilumab, Actoxumab, Adalimumab, Adecatumumab, Aducanumab, Afasevikumab, Afelimomab, Afutuzumab, Alacizumab pegol, ALD518, ALD403, Alemtuzumab, Alirocumab, Altumomab pentetate, Amatuximab, AMG 334, Anatumomab mafenatox, Anetumab ravtansine, Anifrolumab, Anrukinzumab, Apolizumab, Arcitumomab, Ascrinvacumab, Aselizumab, Atezolizumab, Atinumab, Atlizumab, Atorolimumab, Avelumab, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cergutuzumab amunaleukin, Certolizumab pegol, Cetuximab, Citatuzumab bogatox, Cixutumumab, Clazakizumab, Clenoliximab, Clivatuzumab tetraxetan, Codrituzumab, Coltuximab ravtansine, Conatumumab, Concizumab, CR6261, Crenezumab, Crotedumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dinutuximab, Diridavumab, Domagrozumab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Emibetuzumab, Emicizumab, Enavatuzumab, Enfortumab vedotin, Enlimomab pegol, Enoblituzumab, Enokizumab, Enoticumab, Ensituximab, Epitumomab cituxetan, Epratuzumab, Erenumab, Erlizumab, Ertumaxomab, Etaracizumab, Etrolizumab, Evinacumab, Evolocumab, Exbivirumab, Fanolesomab, Faralimomab, Farletuzumab, Fasinumab, FBTA05, Felvizumab, Fezakinumab, Fibatuzumab, Ficlatuzumab, Figitumumab, Firivumab, Flanvotumab, Fletikumab, Fontolizumab, Foralumab, Foravirumab, Fresolimumab, Fulranumab, Futuximab, Galcanezumab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Idarucizumab, Igovomab, IMA-638, IMAB362, Imalumab, Imciromab, Imgatuzumab, Inclacumab, Indatuximab ravtansine, Indusatumab vedotin, Inebilizumab, Infliximab, Inolimomab, Inotuzumab ozogamicin, Intetumumab, Ipilimumab, Iratumumab, Isatuximab, Itolizumab, Ixekizumab, Keliximab, Labetuzumab, Lambrolizumab, Lampalizumab, Lanadelumab, Landogrozumab, Laprituximab emtansine, LBR-101/PF0442g7429, Lebrikizumab, Lemalesomab, Lendalizumab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, LY2951742, Mapatumumab, Margetuximab, Maslimomab, Matuzumab, Mavrilimumab, Mepolizumab, Metelimumab, Milatuzumab, Minretumomab, Mirvetuximab soravtansine, Mitumomab, Mogamulizumab, Monalizumab, Morolimumab, Motavizumab, Moxetumomab pasudotox, Muromonab-CD3, Nacolomab tafenatox, Nam ilumab, Naptumomab estafenatox, Naratuximab emtansine, Narnatumab, Natalizumab, Navicixizumab, Navivumab, Nebacumab, Necitumumab, Nemolizumab, Nerelimomab, Nesvacumab, Nimotuzumab, Nivolumab, Nofetumomab merpentan, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oportuzumab monatox, Oregovomab, Orticumab, Otelixizumab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Prezalizumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Reslizumab, Rilotumumab, Rinucumab, Risankizumab, Rituximab, Rivabazumab pegol, Robatumumab, Roledumab, Romosozumab, Rontalizumab, Rovalpituzumab tesirine, Rovelizumab, Ruplizumab, Sacituzumab govitecan, Samalizumab, Sapelizumab, Sarilumab, Satumomab pendetide, Secukinumab, Seribantumab, Setoxaximab, Sevirumab, SGN-CD19A, SGN-CD33A, Sibrotuzumab, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tamtuvetmab, Tanezumab, Taplitumomab paptox, Tarextumab, Tefibazumab, Telimomab aritox, Tenatumomab, Tenelixmab, Teplizumab, Teprotumumab, Tesidolumab, Tetulomab, Tezepelumab, TGN1412, Ticilimumab, Tigatuzumab, Tildrakizumab, Timolumab, Tisotumab vedotin, TNX-650, Tocilizumab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Vobarilizumab, Volociximab, Vorsetuzumab mafodotin, Votumumab, Xentuzumab, Zalutumumab, Zanolimumab, Zatuximab, Ziralimumab, and Zolimomab aritox or combinations thereof.

Examples of vaccines developed for viral diseases include but are not limited to: Hepatitis A vaccine, Hepatitis B vaccine, Hepatitis E vaccine, HPV vaccine, Influenza vaccine, Japanese encephalitis vaccine, MMR vaccine, MMRV vaccine, Polio vaccine, Rabies vaccine, Rotavirus vaccine, Varicella vaccine, Shingles vaccine, Smallpox vaccine, Yellow Fever vaccine, Adenovirus vaccine, Coxsackie B virus vaccine, Cytomegalovirus vaccine, Dengue vaccine for humans, Eastern Equine encephalitis virus vaccine for humans, Ebola vaccine, Enterovirus 71 vaccine, Epstein-Barr vaccine, Hepatitis C vaccine, HIV vaccine, HTLV-1 T-lymphotropic leukemia vaccine for humans, Marburg virus disease vaccine, Norovirus vaccine, Respiratory syncytial virus vaccine for humans, Severe acute respiratory syndrome (SARS) vaccine, West Nile virus vaccine for humans; Examples of bacterial diseases include but are not limited to: Anthrax vaccines, DPT vaccine, Q fever vaccine, Hib vaccine, Tuberculosis (BCG) vaccine, Meningococcal vaccine, Typhoid vaccine, Pneumococcal conjugate vaccine, Pneumococcal polysaccharide vaccine, Cholera vaccine, Caries vaccine, Ehrlichiosis vaccine, Leprosy vaccine, Lyme disease vaccine, *Staphylococcus aureus* vaccine, *Streptococcus pyogenes* vaccine, Syphilis vaccine, Tularemia vaccine, *Yersinia pestis* vaccine; Examples of parasitic diseases include but are not limited to: Malaria vaccine, Schistosomiasis vaccine, Chagas disease vaccine, Hookworm vaccine, Onchocerciasis river blindness vaccine for humans, Trypanosomiasis vaccine, Visceral leishmaniasis vaccine; Examples of non-infectious diseases include but are not limited to: Alzheimer's disease amyloid protein vaccine, Breast cancer vaccine, Ovarian cancer vaccine, Prostate cancer vaccine, Talimogene laherparepvec (T-VEC); also vaccines including but not limited to the following trade names: ACAM2000, ActHIB, Adacel, Afluria, AFLURIA QUADRIVALENT, Agriflu, BCG Vaccine, BEXSERO, Biothrax, Boostrix, Cervarix, Comvax, DAPTACEL, DECAVAC, Engerix-B, FLUAD, Fluarix, Fluarix Quadrivalent, Flublok, Flucelvax, Flucelvax Quadrivalent, FluLaval, FluMist, FluMist Quadrivalent, Fluvirin, Fluzone Quadrivalent, Fluzone, Fluzone High-Dose and Fluzone Intradermal, Gardasil, Gardasil 9, Havrix, Hiberix, Imovax, Infanrix, IPOL, Ixiaro, JE-Vax, KINRIX, Menactra, MenHibrix, Menomune-A/CMW-135, Menveo, M-M-R II, M-M-Vax, Pediarix, PedvaxHIB, Pentacel, Pneumovax 23, Poliovax, Prevnar, Prevnar 13, ProQuad, Quadracel, Quadrivalent, RabAvert, Recombivax HB, ROTARIX, RotaTeq, TEN IVAC, TICE BCG, Tripedia, TRUMENBA, Twinrix, TYPHIM Vi, VAQTA, Varivax, Vaxchora, Vivotif, YF-Vax, Zostavax, and combinations thereof.

Examples of injectable drugs include but are not limited to: Ablavar (Gadofosveset Trisodium Injection), Abarelix Depot, Abobotulinumtoxin A Injection (Dysport), ABT-263, ABT-869, ABX-EFG, Accretropin (Somatropin Injection), Acetadote (Acetylcysteine Injection), Acetazolamide Injection (Acetazolamide Injection), Acetylcysteine Injection (Acetadote), Actemra (Tocilizumab Injection), Acthrel (Corticorelin Ovine Triflutate for Injection), Actummune, Activase, Acyclovir for Injection (Zovirax Injection), Adacel, Adalimumab, Adenoscan (Adenosine Injection), Adenosine Injection (Adenoscan), Adrenaclick, AdreView (Iobenguane 1123 Injection for Intravenous Use), Afluria, Ak-Fluor (Fluorescein Injection), Aldurazyme (Laronidase), Alglucerase Injection (Ceredase), Alkeran Injection (Melphalan Hcl Injection), Allopurinol Sodium for Injection (Aloprim), Aloprim (Allopurinol Sodium for Injection), Alprostadil, Alsuma (Sumatriptan Injection), ALTU-238, Amino Acid Injections, Aminosyn, Apidra, Apremilast, Alprostadil Dual Chamber System for Injection (Caverject Impulse), AMG 009, AMG 076, AMG 102, AMG 108, AMG 114, AMG 162, AMG 220, AMG 221, AMG 222, AMG 223, AMG 317, AMG 379, AMG 386, AMG 403, AMG 477, AMG 479, AMG 517, AMG 531, AMG 557, AMG 623, AMG 655, AMG 706, AMG 714, AMG 745, AMG 785, AMG 811, AMG 827, AMG 837, AMG 853, AMG 951, Amiodarone HCl Injection (Amiodarone HCl Injection), Amobarbital Sodium Injection (Amytal Sodium), Amytal Sodium (Amobarbital Sodium Injection), Anakinra, Anti-Abeta, Anti-Beta7, Anti-Beta20, Anti-CD4, Anti-CD20, Anti-CD40, Anti-IFNalpha, Anti-IL13, Anti-OX40L, Anti-oxLDS, Anti-NGF, Anti-NRP1, Arixtra, Amphadase (Hyaluronidase Inj), Ammonul (Sodium Phenylacetate and Sodium Benzoate Injection), Anaprox, Anzemet Injection (Dolasetron Mesylate Injection), Apidra (Insulin Glulisine [rDNA origin] Inj), Apomab, Aranesp (darbepoetin alfa), Argatroban (Argatroban Injection), Arginine Hydrochloride Injection (R-Gene 10, Aristocort, Aristospan, Arsenic Trioxide Injection (Trisenox), Articane HCl and Epinephrine Injection (Septocaine), Arzerra (Ofatumumab Injection), Asclera (Polidocanol Injection), Ataluren, Ataluren-DMD, Atenolol Inj (Tenormin I.V. Injection), Atracurium Besylate Injection (Atracurium Besylate Injection), Avastin, Azactam Injection (Aztreonam Injection), Azithromycin (Zithromax Injection), Aztreonam Injection (Azactam Injection), Baclofen Injection (Lioresal Intrathecal), Bacteriostatic Water (Bacteriostatic Water for Injection), Baclofen Injection (Lioresal Intrathecal), Bal in Oil Ampules (Dimercarprol Injection), BayHepB, BayTet, Benadryl, Bendamustine Hydrochloride Injection (Treanda), Benztropine Mesylate Injection (Cogentin), Betamethasone Injectable Suspension (Celestone Soluspan), Bexxar, Bicillin C-R 900/300 (Penicillin G Benzathine and Penicillin G Procaine Injection), Blenoxane (Bleomycin Sulfate Injection), Bleomycin Sulfate Injection (Blenoxane), Boniva Injection (Ibandronate Sodium Injection), Botox Cosmetic (OnabotulinumtoxinA for Injection), BR3-FC, Bravelle (Urofollitropin Injection), Bretylium (Bretylium Tosylate Injection), Brevital Sodium (Methohexital Sodium for Injection), Brethine, Briobacept, BTT-1023, Bupivacaine HCl, Byetta, Ca-DTPA (Pentetate Calcium Trisodium Inj), Cabazitaxel Injection (Jevtana), Caffeine Alkaloid (Caffeine and Sodium Benzoate Injection), Calcijex Injection (Calcitrol), Calcitrol (Calcijex Injection), Calcium Chloride (Calcium Chloride Injection 10%), Calcium Disodium Versenate (Edetate Calcium Disodium Injection), Campath (Alemtuzumab), Camptosar Injection (Irinotecan Hydrochloride), Canakinumab Injection (Ilaris), Capastat Sulfate (Capreomycin for Injection), Capreomycin for Injection (Capastat Sulfate), Cardiolite (Prep kit for Technetium Tc99 Sestamibi for Injection), Carticel, Cathflo, Cefazolin and Dextrose for Injection (Cefazolin Injection), Cefepime Hydrochloride, Cefotaxime, Ceftriaxone, Cerezyme, Carnitor Injection, Caverject, Celestone Soluspan, Celsior, Cerebyx (Fosphenytoin Sodium Injection), Ceredase (Alglucerase Injection), Ceretec (Technetium Tc99m Exametazime Injection), Certolizumab, CF-101, Chloramphenicol Sodium Succinate (Chloramphenicol Sodium Succinate Injection), Chloramphenicol Sodium Succinate Injection (Chloramphenicol Sodium Succinate), Cholestagel (Colesevelam HCL), Choriogonadotropin Alfa Injection (Ovidrel), Cimzia, Cisplatin (Cisplatin Injection), Clolar (Clofarabine Injection), Clomiphine Citrate, Clonidine Injection (Duraclon), Cogentin (Benztropine Mesylate Injection), Colistimethate Injection (Coly-Mycin M), Coly-Mycin M (Colistimethate Injection), Compath, Conivaptan Hcl Injection (Vaprisol), Conjugated Estrogens for Injection (Premarin Injection), Copaxone, Corticorelin Ovine Triflutate for Injection (Acthrel), Corvert (Ibutilide Fumarate Injection), Cubicin (Daptomycin Injection), CF-101, Cyanokit (Hydroxocobalamin for Injection), Cytarabine Liposome Injection (DepoCyt), Cyanocobalamin, Cytovene (ganciclovir), D.H.E. 45, Dacetuzumab, Dacogen (Decitabine Injection), Dalteparin, Dantrium IV (Dantrolene Sodium for Injection), Dantrolene Sodium for Injection (Dantrium IV), Daptomycin Injection (Cubicin), Darbepoietin Alfa, DDAVP Injection (Desmopressin Acetate Injection), Decavax, Decitabine Injection (Dacogen), Dehydrated Alcohol (Dehydrated Alcohol Injection), Denosumab Injection (Prolia), Delatestryl, Delestrogen, Delteparin Sodium, Depacon (Valproate Sodium Injection), Depo Medrol (Methylprednisolone Acetate Injectable Suspension), DepoCyt (Cytarabine Liposome Injection), DepoDur (Morphine Sulfate XR Liposome Injection), Desmopressin Acetate Injection (DDAVP Injection), Depo-Estradiol, Depo-Provera 104 mg/mL, Depo-Provera 150 mg/mL, Depo-Testosterone, Dexrazoxane for Injection, Intravenous Infusion Only (Totect), Dextrose/Electrolytes, Dextrose and Sodium Chloride Inj (Dextrose 5% in 0.9% Sodium Chloride), Dextrose, Diazepam Injection (Diazepam Injection), Digoxin Injection (Lanoxin Injection), Dilaudid-HP (Hydromorphone Hydrochloride Injection), Dimercarprol Injection (Bal in Oil Ampules), Diphenhydramine Injection (Benadryl Injection), Dipyridamole Injection (Dipyridamole Injection), DMOAD, Docetaxel for Injection (Taxotere), Dolasetron Mesylate Injection (Anzemet Injection), Doribax (Doripenem for Injection), Doripenem for Injection (Doribax), Doxercalciferol Injection (Hectorol Injection), Doxil (Doxorubicin Hcl Liposome Injection), Doxorubicin Hcl Liposome Injection (Doxil), Duraclon (Clonidine Injection), Duramorph (Morphine Injection), Dysport (Abobotulinumtoxin A Injection), Ecallantide Injection (Kalbitor), EC-Naprosyn (naproxen), Edetate Calcium Disodium Injection (Calcium Disodium Versenate), Edex (Alprostadil for Injection), Engerix, Edrophonium Injection (Enlon), Eliglustat Tartate, Eloxatin (Oxaliplatin Injection), Emend Injection (Fosaprepitant Dimeglumine Injection), Enalaprilat Injection (Enalaprilat Injection), Enlon (Edrophonium Injection), Enoxaparin Sodium Injection (Lovenox), Eovist (Gadoxetate Disodium Injection), Enbrel (etanercept), Enoxaparin, Epicel, Epinepherine, Epipen, Epipen Jr., Epratuzumab, Erbitux, Ertapenem Injection (Invanz), Erythropoieten, Essential Amino Acid Injection (Nephramine), Estradiol Cypionate, Estradiol Valerate, Etanercept, Exenatide Injection (Byetta), Evlotra, Fabrazyme (Adalsidase beta), Famotidine Injection, FDG (Fludeoxyglucose F 18 Injection), Feraheme (Ferumoxytol Injection), Feridex I.V. (Ferumoxides Injectable Solution), Fertinex, Ferumoxides Injectable Solution (Feridex I.V.), Ferumoxytol Injection (Feraheme), Flagyl Injection (Metronidazole Injection), Fluarix, Fludara (Fludarabine Phosphate), Fludeoxyglucose F 18 Injection (FDG), Fluorescein Injection (Ak-Fluor), Follistim AQ Cartridge (Follitropin Beta Injection), Follitropin Alfa Injection (Gonal-f RFF), Follitropin Beta Injection (Follistim AQ Cartridge), Folotyn (Pralatrexate Solution for Intravenous Injection), Fondaparinux, Forteo (Teriparatide (rDNA origin) Injection), Fostamatinib, Fosaprepitant Dimeglumine Injection (Emend Injection), Foscarnet Sodium Injection (Foscavir), Foscavir (Foscarnet Sodium Injection), Fosphenytoin Sodium Injection (Cerebyx), Fospropofol Disodium Injection (Lusedra), Fragmin, Fuzeon (enfuvirtide), GA101, Gadobenate Dimeglumine Injection (Multihance), Gadofosveset Trisodium Injection (Ablavar), Gadoteridol Injection Solution (ProHance), Gadoversetamide Injection (OptiMARK), Gadoxetate Disodium Injection (Eovist), Ganirelix (Ganirelix Acetate Injection), Gardasil, GC1008, GDFD, Gemtuzumab Ozogamicin for Injection (Mylotarg), Genotropin, Gentamicin Injection, GENZ-112638, Golimumab Injection (Simponi Injection), Gonal-f RFF (Follitropin Alfa Injection), Granisetron Hydrochloride (Kytril Injection), Gentamicin Sulfate, Glatiramer Acetate, Glucagen, Glucagon, HAE1, Haldol (Haloperidol Injection), Havrix, Hectorol Injection (Doxercalciferol Injection), Hedgehog Pathway Inhibitor, Heparin, Herceptin, hG-CSF, Humalog, Human Growth Hormone, Humatrope, HuMax, Humegon, Humira, Humulin, Ibandronate Sodium Injection (Boniva Injection), Ibuprofen Lysine Injection (NeoProfen), Ibutilide Fumarate Injection (Corvert), Idamycin PFS (Idarubicin Hydrochloride Injection), Idarubicin Hydrochloride Injection (Idamycin PFS), Ilaris (Canakinumab Injection), Imipenem and Cilastatin for Injection (Primaxin I.V.), Imitrex, Incobotulinumtoxin A for Injection (Xeomin), Increlex (Mecasermin [rDNA origin] Injection), Indocin IV (Indomethacin Inj), Indomethacin Inj (Indocin IV), Infanrix, Innohep, Insulin, Insulin Aspart [rDNA origin] Inj (NovoLog), Insulin Glargine [rDNA origin] Injection (Lantus), Insulin Glulisine [rDNA origin] Inj (Apidra), Interferon alfa-2b, Recombinant for Injection (Intron A), Intron A (Interferon alfa-2b, Recombinant for Injection), Invanz (Ertapenem Injection), Invega Sustenna (Paliperidone Palmitate Extended-Release Injectable Suspension), Invirase (saquinavir mesylate), Iobenguane 1123 Injection for Intravenous Use (AdreView), Iopromide Injection (Ultravist), Ioversol Injection (Optiray Injection), Iplex (Mecasermin Rinfabate [rDNA origin] Injection), Iprivask, Irinotecan Hydrochloride (Camptosar Injection), Iron Sucrose Injection (Venofer), Istodax (Romidepsin for Injection), Itraconazole Injection (Sporanox Injection), Jevtana (Cabazitaxel Injection), Jonexa, Kalbitor (Ecallantide Injection), KCL in D5NS (Potassium Chloride in 5% Dextrose and Sodium Chloride Injection), KCL in D5W, KCL in NS, Kenalog 10 Injection (Triamcinolone Acetonide Injectable Suspension), Kepivance (Paliferm in), Keppra Injection (Levetiracetam), Keratinocyte, KFG, Kinase Inhibitor, Kineret (Anakinra), Kinlytic (Urokinase Injection), Kinrix, Klonopin (clonazepam), Kytril Injection (Granisetron Hydrochloride), lacosamide Tablet and Injection (Vimpat), Lactated Ringer's, Lanoxin Injection (Digoxin Injection), Lansoprazole for Injection (Prevacid I.V.), Lantus, Leucovorin Calcium (Leucovorin Calcium Injection), Lente (L), Leptin, Levemir, Leukine Sargramostim, Leuprolide Acetate, Levothyroxine, Levetiracetam (Keppra Injection), Lovenox, Levocarnitine Injection (Carnitor Injection), Lexiscan (Regadenoson Injection), Lioresal Intrathecal (Baclofen Injection), Liraglutide [rDNA] Injection (Victoza), Lovenox (Enoxaparin Sodium Injection), Lucentis (Ranibizumab Injection), Lumizyme, Lupron (Leuprolide Acetate Injection), Lusedra (Fospropofol Disodium Injection), Maci, Magnesium Sulfate (Magnesium Sulfate Injection), Mannitol Injection (Mannitol IV), Marcaine (Bupivacaine Hydrochloride and Epinephrine Injection), Maxipime (Cefepime Hydrochloride for Injection), MDP Multidose Kit of Technetium Injection (Technetium Tc99m Medronate Injection), Mecasermin [rDNA origin] Injection (Increlex), Mecasermin Rinfabate [rDNA origin] Injection (Iplex), Melphalan Hcl Injection (Alkeran Injection), Methotrexate, Menactra, Menopur (Menotropins Injection), Menotropins for Injection (Repronex), Methohexital Sodium for Injection (Brevital Sodium), Methyldopate Hydrochloride Injection, Solution (Methyldopate Hcl), Methylene Blue (Methylene Blue Injection), Methylprednisolone Acetate Injectable Suspension (Depo Medrol), MetMab, Metoclopramide Injection (Reglan Injection), Metrodin (Urofollitropin for Injection), Metronidazole Injection (Flagyl Injection), Miacalcin, Midazolam (Midazolam Injection), Mimpara (Cinacalet), Minocin Injection (Minocycline Inj), Minocycline Inj (Minocin Injection), Mipomersen, Mitoxantrone for Injection Concentrate (Novantrone), Morphine Injection (Duramorph), Morphine Sulfate XR Liposome Injection (DepoDur), Morrhuate Sodium (Morrhuate Sodium Injection), Motesanib, Mozobil (Plerixafor Injection), Multihance (Gadobenate Dimeglumine Injection), Multiple Electrolytes and Dextrose Injection, Multiple Electrolytes Injection, Mylotarg (Gemtuzumab Ozogamicin for Injection), Myozyme (Alglucosidase alfa), Nafcillin Injection (Nafcillin Sodium), Nafcillin Sodium (Nafcillin Injection), Naltrexone XR Inj (Vivitrol), Naprosyn (naproxen), NeoProfen (Ibuprofen Lysine Injection), Nandrol Decanoate, Neostigmine Methylsulfate (Neostigmine Methylsulfate Injection), NEO-GAA, NeoTect (Technetium Tc 99m Depreotide Injection), Nephramine (Essential Amino Acid Injection), Neulasta (pegfilgrastim), Neupogen (Filgrastim), Novolin, Novolog, NeoRecormon, Neutrexin (Trimetrexate Glucuronate Inj), NPH (N), Nexterone (Amiodarone HCl Injection), Norditropin (Somatropin Injection), Normal Saline (Sodium Chloride Injection), Novantrone (Mitoxantrone for Injection Concentrate), Novolin 70/30 Innolet (70% NPH, Human Insulin Isophane Suspension and 30% Regular, Human Insulin Injection), NovoLog (Insulin Aspart [rDNA origin] Inj), Nplate (romiplostim), Nutropin (Somatropin (rDNA origin) for Inj), Nutropin AQ, Nutropin Depot (Somatropin (rDNA origin) for Inj), Octreotide Acetate Injection (Sandostatin LAR), Ocrelizumab, Ofatumumab Injection (Arzerra), Olanzapine Extended Release Injectable Suspension (Zyprexa Relprevv), Omnitarg, Omnitrope (Somatropin [rDNA origin] Injection), Ondansetron Hydrochloride Injection (Zofran Injection), OptiMARK (Gadoversetamide Injection), Optiray Injection (Ioversol Injection), Orencia, Osmitrol Injection in Aviva (Mannitol Injection in Aviva Plastic Vessel 250), Osmitrol Injection in Viaflex (Mannitol Injection in Viaflex Plastic Vessel 250), Osteoprotegrin, Ovidrel (Choriogonadotropin Alfa Injection), Oxacillin (Oxacillin for Injection), Oxaliplatin Injection (Eloxatin), Oxytocin Injection (Pitocin), Paliperidone Palmitate Extended-Release Injectable Suspension (Invega Sustenna), Pamidronate Disodium Injection (Pamidronate Disodium Injection), Panitumumab Injection for Intravenous Use (Vectibix), Papaverine Hydrochloride Injection (Papaverine Injection), Papaverine Injection (Papaverine Hydrochloride Injection), Parathyroid Hormone, Paricalcitol Injection Fliptop Vial (Zemplar Injection), PARP Inhibitor, Pediarix, PEGIntron, Peginterferon, Pegfilgrastim, Penicillin G Benzathine and Penicillin G Procaine, Pentetate Calcium Trisodium Inj (Ca-DTPA), Pentetate Zinc Trisodium Injection (Zn-DTPA), Pepcid Injection (Famotidine Injection), Pergonal, Pertuzumab, Phentolamine Mesylate (Phentolamine Mesylate for Injection), Physostigmine Salicylate (Physostigmine Salicylate (injection)), Physostigmine Salicylate (injection) (Physostigmine Salicylate), Piperacillin and Tazobactam Injection (Zosyn), Pitocin (Oxytocin Injection), Plasma-Lyte 148 (Multiple Electrolytes Inj), Plasma-Lyte 56 and Dextrose (Multiple Electrolytes and Dextrose Injection in Viaflex, Plastic Vessel 250), PlasmaLyte, Plerixafor Injection (Mozobil), Polidocanol Injection (Asclera), Potassium Chloride, Pralatrexate Solution for Intravenous Injection (Folotyn), Pramlintide Acetate Injection (Symlin), Premarin Injection (Conjugated Estrogens for Injection), Prep kit for Technetium Tc99 Sestamibi for Injection (Cardiolite), Prevacid I.V. (Lansoprazole for Injection), Primaxin I.V. (Imipenem and Cilastatin for Injection), Prochymal, Procrit, Progesterone, ProHance (Gadoteridol Injection Solution), Prolia (Denosumab Injection), Promethazine HCl Injection (Promethazine Hydrochloride Injection), Propranolol Hydrochloride Injection (Propranolol Hydrochloride Injection), Quinidine Gluconate Injection (Quinidine Injection), Quinidine Injection (Quinidine Gluconate Injection), R-Gene 10 (Arginine Hydrochloride Injection), Ranibizumab Injection (Lucentis), Ranitidine Hydrochloride Injection (Zantac Injection), Raptiva, Reclast (Zoledronic Acid Injection), Recombivarix HB, Regadenoson Injection (Lexiscan), Reglan Injection (Metoclopramide Injection), Remicade, Renagel, Renvela (Sevelamer Carbonate), Repronex (Menotropins for Injection), Retrovir IV (Zidovudine Injection), rhApo2L/TRAIL, Ringer's and 5% Dextrose Injection (Ringers in Dextrose), Ringer's Injection (Ringers Injection), Rituxan, Rituximab, Rocephin (ceftriaxone), Rocuronium Bromide Injection (Zemuron), Roferon-A (interferon alfa-2a), Romazicon (flumazenil), Romidepsin for Injection (Istodax), Saizen (Somatropin Injection), Sandostatin LAR (Octreotide Acetate Injection), Sclerostin Ab, Sensipar (cinacalcet), Sensorcaine (Bupivacaine HCl Injections), Septocaine (Articane HCl and Epinephrine Injection), Serostim LQ (Somatropin (rDNA origin) Injection), Simponi Injection (Golimumab Injection), Sodium Acetate (Sodium Acetate Injection), Sodium Bicarbonate (Sodium Bicarbonate 5% Injection), Sodium Lactate (Sodium Lactate Injection in AVIVA), Sodium Phenylacetate and Sodium Benzoate Injection (Ammonul), Somatropin (rDNA origin) for Inj (Nutropin), Sporanox Injection (Itraconazole Injection), Stelara Injection (Ustekinumab), Stemgen, Sufenta (Sufentanil Citrate Injection), Sufentanil Citrate Injection (Sufenta), Sumavel, Sumatriptan Injection (Alsuma), Symlin, Symlin Pen, Systemic Hedgehog Antagonist, Synvisc-One (Hylan G-F 20 Single Intra-articular Injection), Tarceva, Taxotere (Docetaxel for Injection), Technetium Tc 99m, Telavancin for Injection (Vibativ), Temsirolimus Injection (Torisel), Tenormin I.V. Injection (Atenolol Inj), Teriparatide (rDNA origin) Injection (Forteo), Testosterone Cypionate, Testosterone Enanthate, Testosterone Propionate, Tev-Tropin (Somatropin, rDNA Origin, for Injection), tgAAC94, Thallous Chloride, Theophylline, Thiotepa (Thiotepa Injection), Thymoglobulin (Anti-Thymocyte Globulin (Rabbit), Thyrogen (Thyrotropin Alfa for Injection), Ticarcillin Disodium and Clavulanate Potassium Galaxy (Timentin Injection), Tigan Injection (Trimethobenzamide Hydrochloride Injectable), Timentin Injection (Ticarcillin Disodium and Clavulanate Potassium Galaxy), TNKase, Tobramycin Injection (Tobramycin Injection), Tocilizumab Injection (Actemra), Torisel (Temsirolimus Injection), Totect (Dexrazoxane for Injection, Intravenous Infusion Only), Trastuzumab-DM1, Travasol (Amino Acids (Injection)), Treanda (Bendamustine Hydrochloride Injection), Trelstar (Triptorelin Pamoate for Injectable Suspension), Triamcinolone Acetonide, Triamcinolone Diacetate, Triamcinolone Hexacetonide Injectable Suspension (Aristospan Injection 20 mg), Triesence (Triamcinolone Acetonide Injectable Suspension), Trimethobenzamide Hydrochloride Injectable (Tigan Injection), Trimetrexate Glucuronate Inj (Neutrexin), Triptorelin Pamoate for Injectable Suspension (Trelstar), Twinject, Trivaris (Triamcinolone Acetonide Injectable Suspension), Trisenox (Arsenic Trioxide Injection), Twinrix, Typhoid Vi, Ultravist (Iopromide Injection), Urofollitropin for Injection (Metrodin), Urokinase Injection (Kinlytic), Ustekinumab (Stelara Injection), Ultralente (U), Valium (diazepam), Valproate Sodium Injection (Depacon), Valtropin (Somatropin Injection), Vancomycin Hydrochloride (Vancomycin Hydrochloride Injection), Vancomycin Hydrochloride Injection (Vancomycin Hydrochloride), Vaprisol (Conivaptan Hcl Injection), VAQTA, Vasovist (Gadofosveset Trisodium Injection for Intravenous Use), Vectibix (Panitumumab Injection for Intravenous Use), Venofer (Iron Sucrose Injection), Verteporfin Inj (Visudyne), Vibativ (Telavancin for Injection), Victoza (Liraglutide [rDNA] Injection), Vimpat (lacosamide Tablet and Injection), Vinblastine Sulfate (Vinblastine Sulfate Injection), Vincasar PFS (Vincristine Sulfate Injection), Victoza, Vincristine Sulfate (Vincristine Sulfate Injection), Visudyne (Verteporfin Inj), Vitamin B-12, Vivitrol (Naltrexone XR Inj), Voluven (Hydroxyethyl Starch in Sodium Chloride Injection), Xeloda, Xenical (orlistat), Xeomin (Incobotulinumtoxin A for Injection), Xolair, Zantac Injection (Ranitidine Hydrochloride Injection), Zemplar Injection (Paricalcitol Injection Fliptop Vial), Zemuron (Rocuronium Bromide Injection), Zenapax (daclizumab), Zevalin, Zidovudine Injection (Retrovir IV), Zithromax Injection (Azithromycin), Zn-DTPA (Pentetate Zinc Trisodium Injection), Zofran Injection (Ondansetron Hydrochloride Injection), Zingo, Zoledronic Acid for Inj (Zometa), Zoledronic Acid Injection (Reclast), Zometa (Zoledronic Acid for Inj), Zosyn (Piperacillin and Tazobactam Injection), Zyprexa Relprevv (Olanzapine Extended Release Injectable Suspension) and combinations thereof.

EXAMPLE

It is to be appreciated that Example 1 was conducted with respect to an insertion tube in a related application, U.S. Patent Publication No. 2019/062959 to Basham, et al. However, it is believed (by one of ordinary skill in the art) that because the mechanism herein is the same as the mechanism described and set forth in U.S. Patent Publication 2019/062959 to Basham, et al., that the surface finish results would also be the same, or of an insignificant difference.

Example 1—Vacuum Chamber Surface Finish

A strip (3 mm×75 mm) of 22 µm cellulose acetate replicating tape (Ted Pella, Inc., Redding CA) was applied to the inner surface of several exemplary insertion tubes. The insertion tubes were formed of stainless steel and were prepared generally according to the teachings of U.S. Pat. No. 10,369,292 to LaRose. The interior of insertion tubes 1 and 2 were surface treated or otherwise finished to reduce or minimize any asperities located within the tubes. The insertion tubes were wetted with acetone and allowed to dry. The strips of cellulose acetate were then removed from the insertion tubes using forceps. The strips were mounted on slides. The replicating tape surfaces were measured on a Keyence VK-X100 3D laser scanning microscope (Keyence Corporation, Osaka, Japan) using a 50× objective (200 µm×270 µm field of view), a 2.5 µm S-filter, a 0.1 mm L-filter cut off wavelength, and a curved surface tilt correction. The average surface roughness ($S_a$) and average kurtosis ($S_{ku}$) were calculated per ISO 25178-2:2012. The data is set forth in Table 1.

Table 1 shows desirable surface parameters for Insertion Tubes 1 and 2, which resulted in successful insertions of the stoppers, as indicated by the helium leak rate and the number of lines observed on the front sealing rib of the stopper. In contrast, Insertion Tubes 3, 4 and 5 did not show desirable surface parameters, and did not result in a successful insertion of the stopper.

TABLE 1

| Insertion Tube | Tube Body | | Transition Zone | Average Number of Lines Observed on the Front Sealing Rib of the Stopper | Average Helium Leak Rate (sccs) |
| --- | --- | --- | --- | --- | --- |
| | Average Surface Roughness $(S_a)$ (nm) | Average Kurtosis $(S_{ku})$ | Average Surface Roughness $(S_a)$(nm) | | |
| Insertion Tube 1 | 46 | 3.1 | 97 | 9 | $7.366 \times 10^{-9}$ |
| Insertion Tube 2 | 101, 103[1] | 3.9, 5.1 | 195, 269 | 1 | $2.077 \times 10^{-9}$ |
| Insertion Tube 3 | 37, 33 | 9.5, 12.8 | 450, 482 | 37 | $2.58 \times 10^{-7}$ |
| Insertion Tube 4 | 40, 121 | 12.9, 13.4 | 428 | 27 | $3.31 \times 10^{-7}$ |
| Insertion Tube 5 | 30, 43 | 8.8, 11.6 | 514 | 22 | $3.16 \times 10^{-8}$ |

[1]In some samples two measurements were reported.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A method comprising:

providing a syringe including a non-lubricated inner surface and a barrel flange;

inserting a non-lubricated stopper that includes a sealing rib into a placement region located at a proximal end of a vacuum chamber, the non-lubricated stopper being at least partially covered by a polymer layer;

creating a seal between a sealing gasket of the vacuum chamber and the barrel flange of the syringe;

applying vacuum through a vacuum port fluidly connected to the non-lubricated barrel and located at a distal end of the vacuum chamber to translate the stopper through the vacuum chamber from the placement region of the vacuum chamber into a proximal end of the non-lubricated barrel;

translating the stopper through the non-lubricated barrel with an insertion rod until a desired headspace between a front edge of the sealing rib and a liquid solution located in the non-lubricated cartridge tube is achieved;

retracting the insertion rod away from the vacuum chamber; and retracting the vacuum chamber away from the non-lubricated barrel.

2. The method of claim 1, wherein the non-lubricated stopper comprises an elastomeric material having the polymer layer thereon.

3. The method of claim 1, wherein the polymer layer comprises an expanded fluoropolymer layer.

4. The method of claim 3, wherein the expanded fluoropolymer layer comprises an expanded polytetrafluoroethylene layer.

5. The method of claim 1, comprising adding the liquid solution to the non-lubricated barrel prior to creating the vacuum seal between the sealing gasket and the barrel flange.

6. The method of claim 1, wherein the liquid solution is a therapeutic substance.

7. The method of claim 6, wherein the therapeutic substance contains therein a biologic, a therapeutic compound, or a combination thereof.

8. The method of claim 1, wherein the vacuum chamber has been electropolished, extrude honed, or a combination thereof.

9. The method of claim 1, wherein at least the stopper, the vacuum chamber, the syringe barrel, the barrel flange, and the insertion pin are free or substantially free of lubricants.

10. The method of claim 1, wherein the vacuum chamber contains a transition zone having a taper angle for transitioning the non-lubricated stopper from the placement region of the vacuum chamber to the proximal end of the barrel.

11. The method of claim 10, wherein the taper angle is between 0.1 degree and 20 degrees.

12. The method of claim 1, wherein the desired headspace ranges from 1 mm to 25 mm.

13. The method of claim 1, wherein the insertion rod includes a pin tip end and the non-lubricated stopper contains therein a cavity to receive the pin tip end.

14. The method of claim 1, wherein the vacuum chamber is positioned above and is aligned with the non-lubricated barrel.

15. The method of claim 1, comprising lowering the vacuum chamber to create the vacuum seal with the non-lubricated barrel.

16. The method of claim 1, wherein the insertion rod and vacuum chamber are retracted simultaneously.

17. The method of claim 1, wherein the insertion rod is retracted prior to retracting the vacuum chamber.

* * * * *